US012673034B2

(12) United States Patent
Brown et al.

(10) Patent No.: US 12,673,034 B2
(45) Date of Patent: Jul. 7, 2026

(54) PEPTIDES, COMPOUNDS, COMPOSITIONS AND METHODS FOR INHIBITING SOX9

(71) Applicants: Arthur Brown, London (CA); CRITICAL OUTCOME TECHNOLOGIES INC., London (CA)

(72) Inventors: Arthur Brown, London (CA); Todd Hryciw, London (CA); Tony Durst, Ottawa (CA); Clinton Threlfall, London (CA)

( * ) Notice: Subject to any disclaimer, the term of this patent is extended or adjusted under 35 U.S.C. 154(b) by 994 days.

(21) Appl. No.: 17/778,124

(22) PCT Filed: Nov. 22, 2019

(86) PCT No.: PCT/CA2019/051677
§ 371 (c)(1),
(2) Date: May 19, 2022

(87) PCT Pub. No.: WO2021/097552
PCT Pub. Date: May 27, 2021

(65) Prior Publication Data

US 2023/0026791 A1 Jan. 26, 2023

(51) Int. Cl.

*A61K 31/167* (2006.01)
*A61K 31/40* (2006.01)
*A61K 31/445* (2006.01)
*A61P 25/00* (2006.01)

(52) U.S. Cl.
CPC ............ *A61K 31/167* (2013.01); *A61K 31/40* (2013.01); *A61K 31/445* (2013.01); *A61P 25/00* (2018.01)

(58) Field of Classification Search
CPC .................................................. A61K 31/167
See application file for complete search history.

(56) References Cited

U.S. PATENT DOCUMENTS

| | | | |
|---|---|---|---|
| 8,642,660 | B2 | 2/2014 | Goldfarb |
| 2008/0059214 | A1 | 3/2008 | Vinberg et al. |
| 2014/0255468 | A1 | 9/2014 | Bancel et al. |

FOREIGN PATENT DOCUMENTS

| | | | |
|---|---|---|---|
| CA | 2667582 | A1 | 5/2008 |
| WO | 2018115302 | A1 | 6/2008 |

OTHER PUBLICATIONS

Fantò, Nicola, et al. "Design, Synthesis, and In Vitro Activity of Peptidomimetic Inhibitors of Myeloid Differentiation Factor 88," Journal of Medicinal Chemistry, vol. 51, No. 5, pp. 1189-1202 (2008).
Patent Cooperation Treaty International Search Report corresponding to International Application No. PCT/CA2019/015677, dated Aug. 17, 2020.
CAS Registry No. 1241022-75-2, Sep. 14, 2010 (Sep. 14, 2010).
CAS Registry No. 940218-78-0, Jun. 29, 2007 (Jun. 29, 2010).
CAS Registry No. 2215548-93-7,Apr. 19, 2018 (Apr. 19, 2018).
CAS Registry No. 1293689-07-2, May 12, 2011 ( Dec. 5, 2011).
CAS Registry No. 1030496-26-4, Jun. 25, 2008 (Jun. 25, 2008).
CAS Registry No. 1030495-83-0, Jun. 25, 2008 (Jun. 25, 2008).
CAS Registry No. 1030458-79-7, Jun. 25, 2008 (Jun. 25, 2008).
CAS Registry No. 1003683-59-7, Feb. 15, 2008 (Feb. 15, 2008).
CAS Registry No. 940521-76-6, Jul. 1, 2007 (Jan. 7, 2007).
CAS Registry No. 940504-94-9, Jul. 1, 2007 (Jan. 7, 2007).
CAS Registry No. 532388-95-7, Jun. 17, 2003 (Jun. 17, 2003).

*Primary Examiner* — Yong S. Chong
(74) *Attorney, Agent, or Firm* — Hoffmann & Baron LLP

(57) ABSTRACT

The present application provides SOX9 inhibitor compounds and compositions and methods of use thereof. In certain aspects, the SOX9 inhibitor is a peptide comprising a portion of the SOX9 dimerization motif. In other aspects, the SOX9 inhibitor is a compound of the general formula I

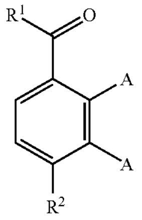

where one A is H and the other is:

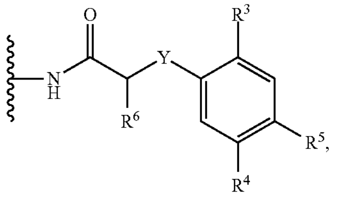

Figure 1:
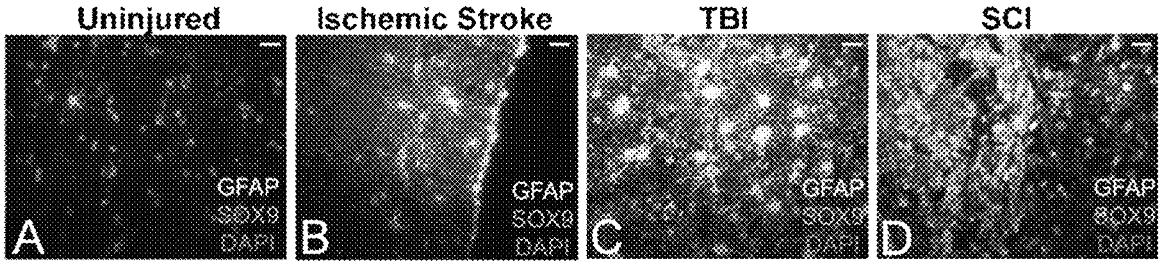

and the remaining substituents are as defined in the application.

13 Claims, 6 Drawing Sheets

Specification includes a Sequence Listing.

SEQUENCE LISTING

```
<160> NUMBER OF SEQ ID NOS: 3

<210> SEQ ID NO 1
<211> LENGTH: 7
<212> TYPE: PRT
<213> ORGANISM: Artificial Sequence
<220> FEATURE:
<223> OTHER INFORMATION: synthetic

<400> SEQUENCE: 1

Ile Arg Glu Ala Val Ser Gln
1               5


<210> SEQ ID NO 2
<211> LENGTH: 20
<212> TYPE: PRT
<213> ORGANISM: Artificial Sequence
<220> FEATURE:
<223> OTHER INFORMATION: synthetic

<400> SEQUENCE: 2

Asp Lys Phe Pro Val Cys Ile Arg Glu Ala Val Ser Gln Val Leu Lys
1               5                   10                  15
```

-continued

```
Gly Tyr Asp Trp
            20


<210> SEQ ID NO 3
<211> LENGTH: 32
<212> TYPE: PRT
<213> ORGANISM: Artificial Sequence
<220> FEATURE:
<223> OTHER INFORMATION: synthetic

<400> SEQUENCE: 3

Asp Lys Phe Pro Val Cys Ile Arg Glu Ala Val Ser Gln Val Leu Lys
1               5                   10                  15

Gly Tyr Asp Trp Lys Tyr Gly Arg Lys Lys Arg Arg Gln Arg Arg Arg
            20                  25                  30
```

PEPTIDES, COMPOUNDS, COMPOSITIONS AND METHODS FOR INHIBITING SOX9

CROSS-REFERENCE TO RELATED APPLICATIONS

This application is a National Phase application of International Application No. PCT/CA2019/051677 filed Nov. 22, 2019, the disclosures of which are incorporated herein by reference.

FIELD OF THE INVENTION

The present application pertains to the field of SOX9 inhibitors. More particularly, the present application relates to compounds and compositions useful for inhibiting SOX9, and methods of manufacture and uses thereof.

INTRODUCTION

Spinal cord injury (SCI) is a catastrophic event that is a major health care issue, causing lifelong disability. In the USA and Canada, more than 12,000 spinal cord injuries occur annually, and about 275,000 people live with permanent, serious disabilities due to SCI (Univ. of Alabama Nat. SCI Stat. Cntr. and the Cdn. Paraplegic Assoc.). Currently, there are no effective treatments for SCI and no therapy or approved strategy for promoting regeneration following other central nervous system (CNS) injury or disease.

Chondroitin sulfate proteoglycans (CSPGs) are a class of extracellular (ECM) macromolecules that share a common structure comprising a central core protein with a number of chondroitin sulfate side chains (Morgenstern et al 2002). Chondroitin sulfate side chain synthesis is initiated by the addition of a xylose onto a serine moiety of the core protein. This function is carried out by the enzymes xylosyltransferase-I and -II (XT-I and XT-II) (Gotting et al 2000). These side chains are subsequently sulfated by chondroitin 4-sulfotransferase (C4ST) (Yamauchi et al 2000). CSPGs are key components of the scar that forms at the lesion site after SCI and of perineuronal nets (PNNs). PNNs are a highly condensed matrix that surrounds the cell bodies and dendrites of some classes of neurons (Celio & Blumcke 1994). CSPGs and other components of the PNNs are produced by both neurons and glia (Galtrey & Fawcett 2007). One suggested function of the CSPGs in PNNs is to stabilize synapses by preventing axonal sprouting onto inappropriate targets after appropriate connections have been made (Galtrey & Fawcett 2007). CSPGs are present in the adult CNS (Bignami et al 1992) and following injury their expression levels increase greatly (Lemons et all 1999 and McKeon et al 1991). In vitro studies have shown that explanted glial tissue expressing CSPGs do not permit neurite extension (McKeon et al 1991) and that chondroitinase treatment of rat spinal cord slices renders glia permissive to neurite outgrowth (Zuo et al 1998). Furthermore, in cultures of primary astrocytes, neurites avoid patches of cells expressing CSPGs (Meiners et al 1995). Specific CSPGs have also been shown to inhibit neurite outgrowth including: NG2 (Dou & Levine 1994), versican (Schmalfeldt et al 2000), neurocan (Friedlander et al 1994), brevican (Yamada et al 1997) and phosphocan (Milev et al 1994). The crucial role played by chondroitin sulfate side chains in axon repulsion is underscored by the observation that digestion of these side chains by the enzyme chondroitinase (Bradbury et al 2002, Caggiano et al 2005, Corvetti & Rossi 2005, Gacia-Alias et al 2009, Huang et al 2006, Ikegami et al 2005, Karimi-Abdolrezaee et al 2010 and Wang et al 2011) or interference with their synthesis by inhibiting XT-I (Grimpe & Silver 2004) increases axonal regeneration in rodent models of SCI. These prior studies suggest that reducing CSPGs improves regeneration in models of SCI.

SOX9 regulates the expression of CSPG core proteins (i.e. ACAN, NCAN) and modulates the expression of CSPG synthesizing enzymes and growth promoting extracellular matrix proteins. Improved locomotor recovery in spinal cord-injured SOX9 knockout mice has been demonstrated (McKillop 2013 and McKillop 2016) suggesting that SOX9 inhibition may be a therapeutically viable strategy to treat spinal cord injury. It has also been found that inhibition of SOX9 or inhibition of calmodulin activity, upon which SOX9's nuclear transport depends (Hanover et al 2009 and McFadden et al 2014), can be effective to treat conditions associated with proteoglycan production or modulation (McKillop 2013).

There remains a need for effective therapies for treating pathological conditions associated with proteoglycan production or modulation, for example nerve damage, especially damage to the central nervous system caused by injury or disease, such as a stroke.

The above information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present application is to provide SOX9 inhibitor compounds and compositions and methods of use thereof. In accordance with an aspect of the present application, there is provided a pharmaceutical composition comprising a SOX9 inhibitor and a pharmaceutically acceptable diluent, carrier or excipient, wherein the SOX9 inhibitor is:

(i) a peptide comprising a sequence of SEQ ID NO:1 or a sequence having at least 80% sequence identity, or at least 85% sequence identity, or at least 90% sequence identity, or at least 95% sequence identity, or at least 99% sequence identity, with the peptide of SEQ ID NO:1; or (ii) an inhibitor compound of formula I:

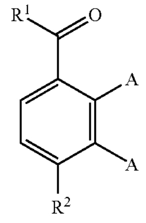

I where:

$R^1$ is $NR^7R^8$, wherein $R^7$ and $R^8$ are each independently a straight or branched $C_1$ to $C_6$ alkyl (e.g., methyl, ethyl, propyl, butyl or isopropyl), or $R^7$ and $R^8$, together with the N atom to which they are attached, form a substituted or unsubstituted heterocyclyl containing one or two heteroatoms selected from N and O (e.g., piperazine, N-methylpiperazine, morpholine, piperidine, or pyrrolidine);

$R^2$ is H, a $C_1$ to $C_6$ alkyl (e.g., methyl), a $C_1$ to $C_6$ alkoxy (e.g., methoxy), or halo (e.g., Cl); and one A is H and the other is:

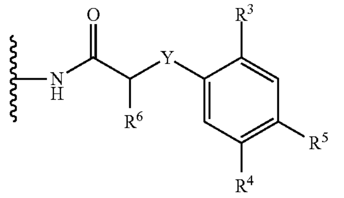

where:

$R^3$ is H or a $C_2$ to $C_6$ alkyl (e.g., ethyl, propyl, butyl or isopropyl;

$R^4$ is H or a $C_1$ to $C_6$ alkyl (e.g., methyl, ethyl, propyl, butyl or isopropyl);

$R^5$ is H, halo (e.g., Cl) or $NCH_2C_6H_5$;

$R^6$ is H or methyl; and

Y is O or $SO_2$, or a pharmaceutically acceptable salt or solvate thereof.

In accordance with certain aspects, there is also provided a use of a SOX 9 inhibitor that is:

(i) a peptide comprising a sequence of SEQ ID NO:1 or a sequence having at least 80% sequence identity, or at least 85% sequence identity, or at least 90% sequence identity, or at least 95% sequence identity, or at least 99% sequence identity, with the peptide of SEQ ID NO:1; or (ii) an inhibitor compound of formula I as defined herein, for treating or preventing a disease or condition characterized by increased SOX9 activity and/or increased CSPG expression, or a disease or disorder that may be ameliorated by decreasing SOX9 or CSPG levels.

In accordance with another aspect, there is provided a method of treating or preventing a disease or condition characterized by increased SOX9 activity and/or increased CSPG expression, or a disease or disorder that may be ameliorated by decreasing SOX9 or CSPG levels, comprising administering to a subject in need thereof a SOX 9 inhibitor that is:

(i) a peptide comprising a sequence of SEQ ID NO:1 or a sequence having at least 80% sequence identity, or at least 85% sequence identity, or at least 90% sequence identity, or at least 95% sequence identity, or at least 99% sequence identity, with the peptide of SEQ ID NO:1; or (ii) an inhibitor compound of formula I as defined herein.

In accordance with another aspect, there is provided a A SOX9 inhibitor that is:

(i) a peptide comprising a sequence of SEQ ID NO:1 or a sequence having at least 80% sequence identity, or at least 85% sequence identity, or at least 90% sequence identity, or at least 95% sequence identity, or at least 99% sequence identity, with the peptide of SEQ ID NO:1; or (ii) a compound of formula I as defined herein.

BRIEF DESCRIPTION OF TABLES AND FIGURES

Figure 2:
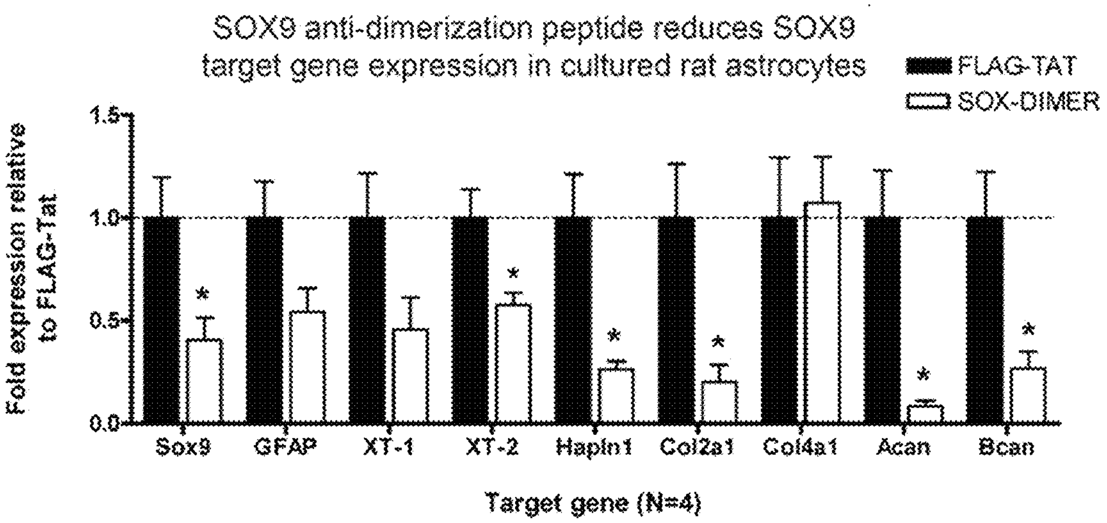
Figure 3:
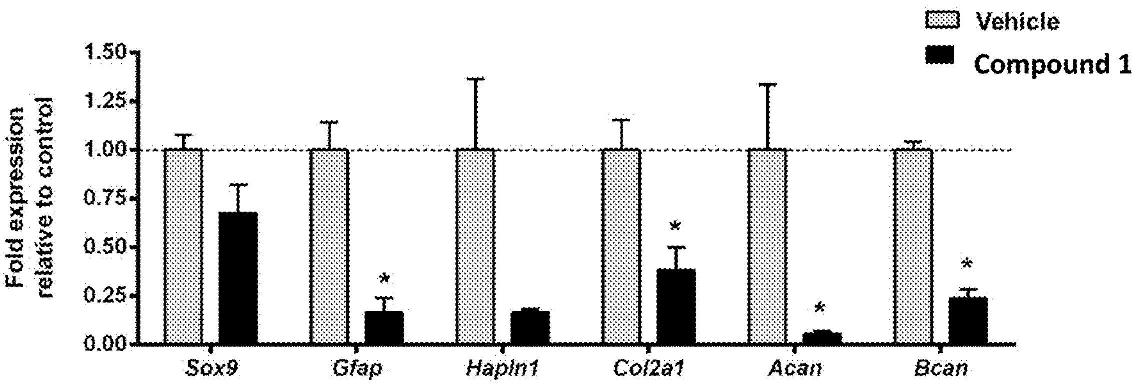
Figure 4:
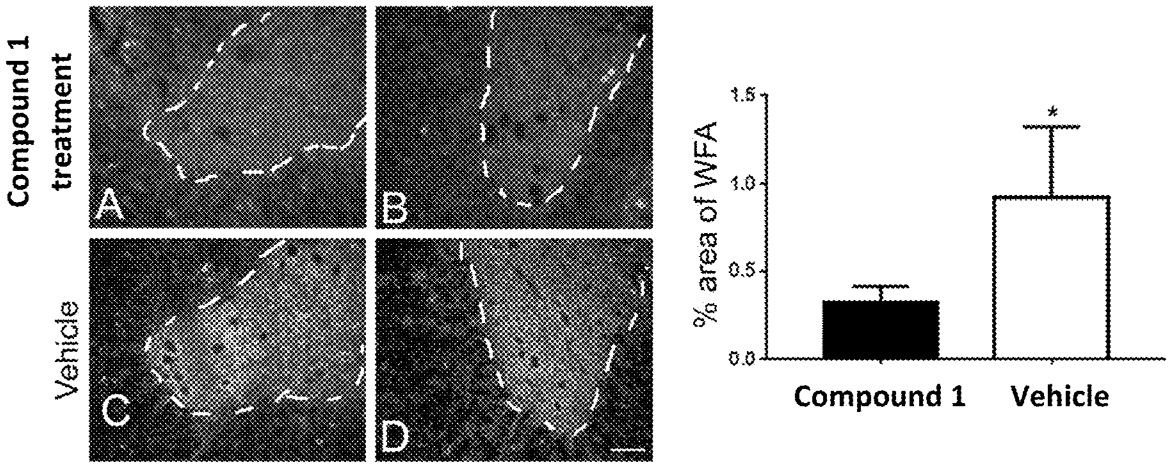
Figure 5:
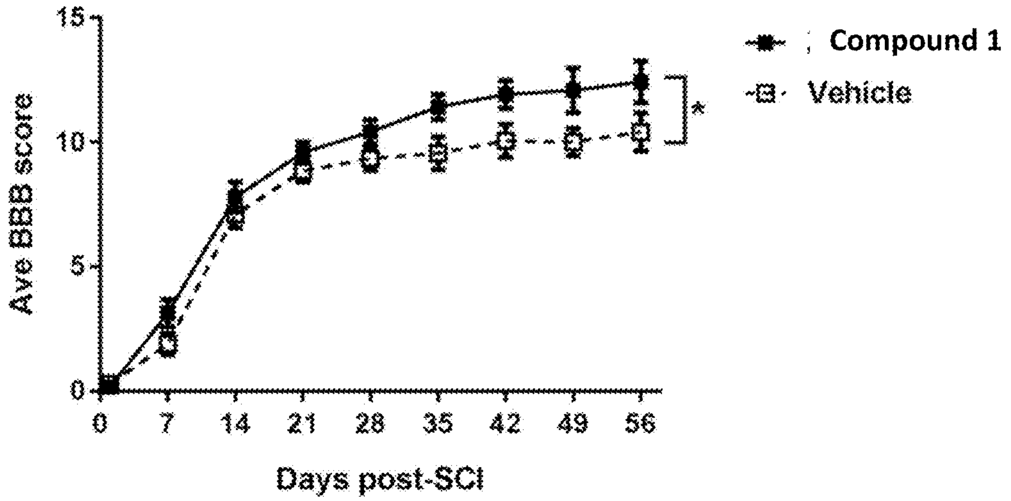
Figure 6:
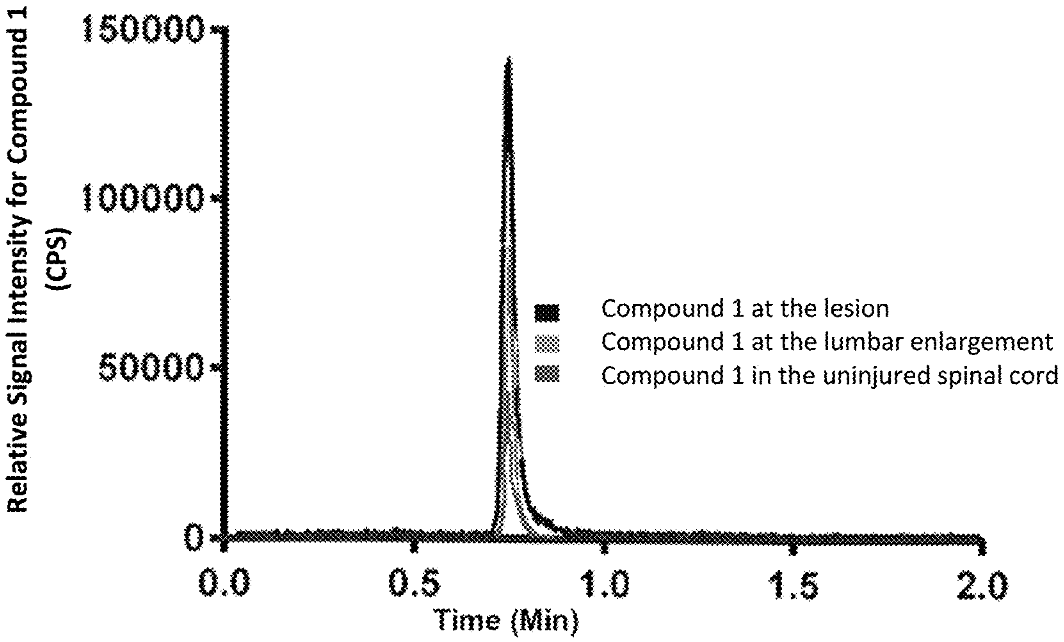
Figure 7:
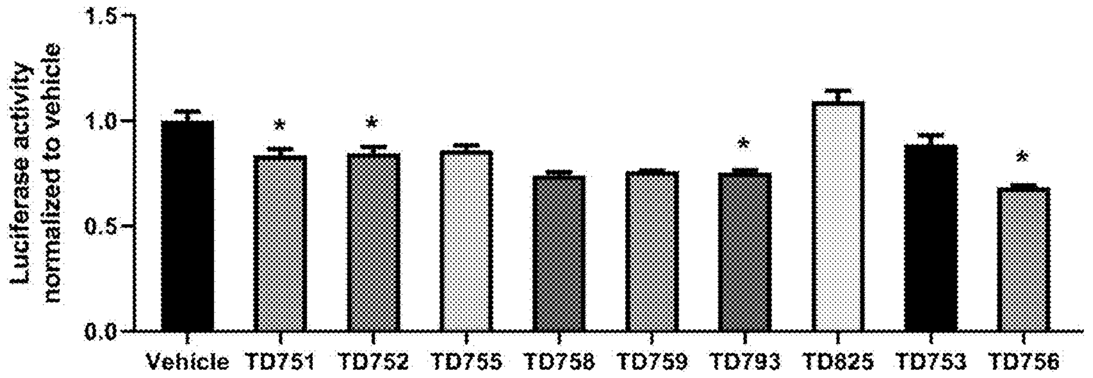
Figure 8:
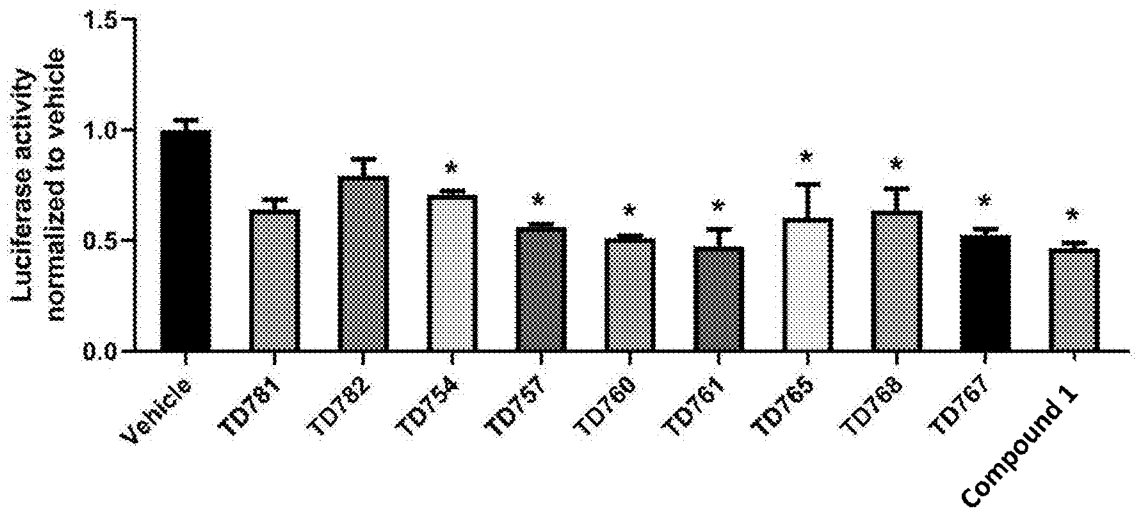
Figure 9:
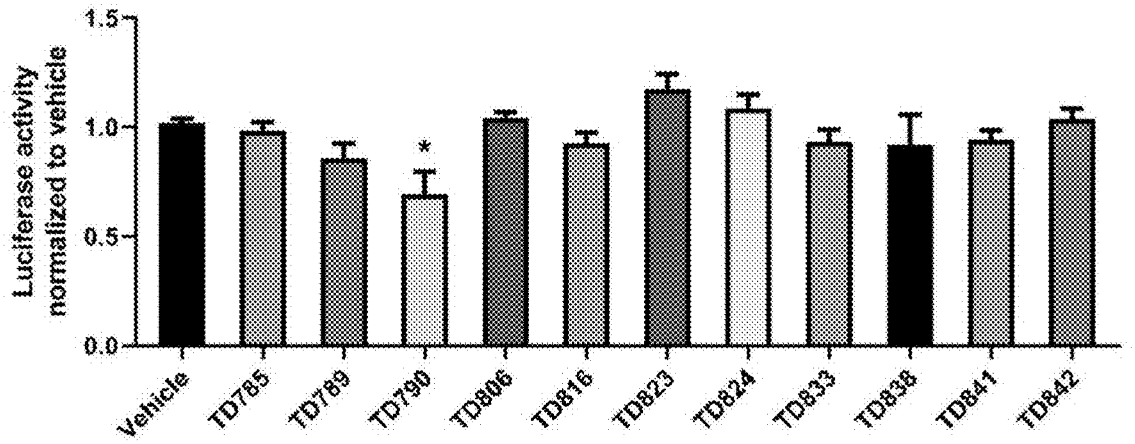
Figure 10:
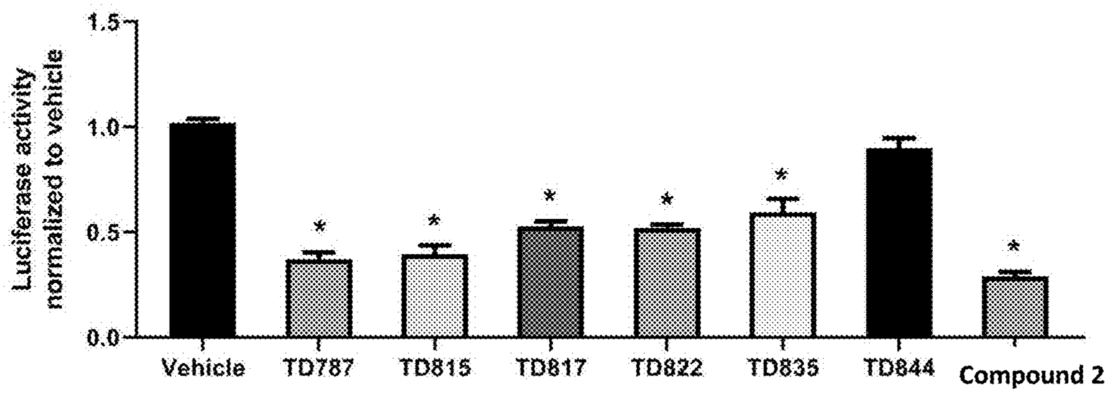
Figure 11:
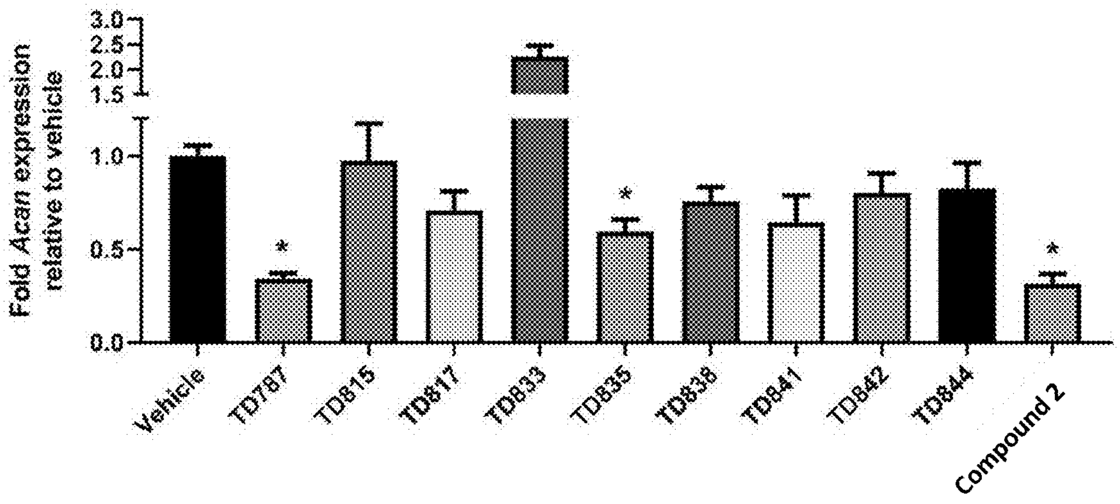
Figure 12:
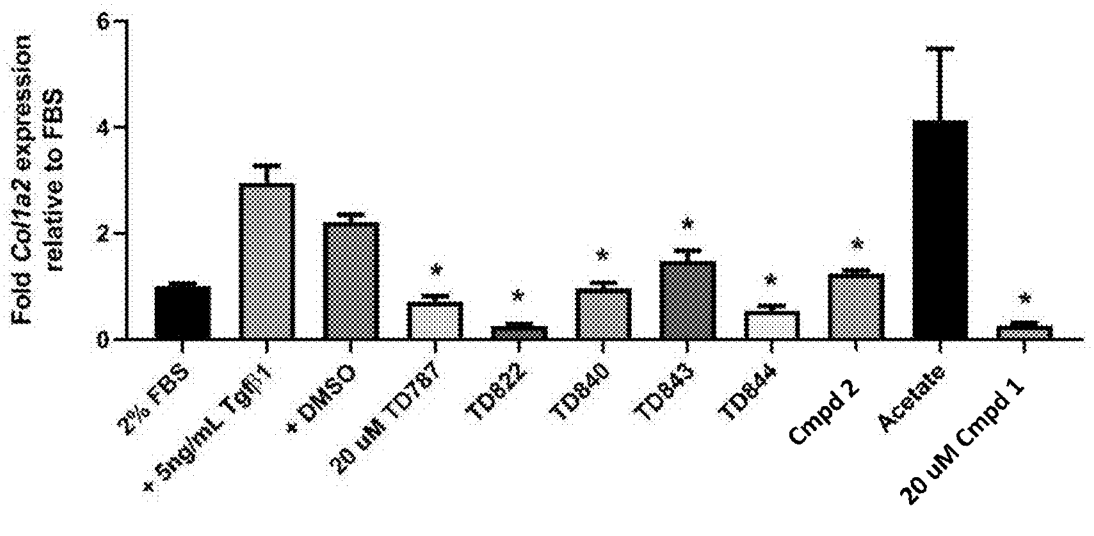

For a better understanding of the application as described herein, as well as other aspects and further features thereof, reference is made to the following description which is to be used in conjunction with the accompanying drawings, where:

FIG. 1 depicts images of brain (A-C) and spinal cord sections from human subjects that have been stained with a combination of antibodies to GFAP, SOX9 and DAPI; the images show that SOX9 expression is seen in human brains after stroke (B), traumatic brain injury (C) and spinal cord injury (D);

FIG. 2 graphically depicts results from treatment of two-week old rat astrocytes for 48 h (hours) with 10 μM SOX-DIMER (white), which show decreased SOX9 target gene expression compared to control (FLAG-Tat) peptide-treated cultures (black) (* indicates statistical significance $P<0.05$, two-tailed t-test; N=4);

FIG. 3 graphically depicts results from treatment of primary astrocyte cultures with vehicle (grey bars), or 10 μM compound 1 (black bars) for 48 h, which demonstrated a decrease in SOX9 target gene expression in primary astrocytes from treatment with compound 1 (* indicates statistical significance $P<0.05$, Student's t-test; n=4);

FIG. 4 shows that compound 1 reduces CSPG levels in the ventral horn of spinal cord injured rats; CSPGs in perineuronal nets were detected by staining sections from control and compound 1-treated rats with biotinylated-WFA followed by a streptavidin Alex 488™ conjucated, where A-D are representative photomicrographs of the WFA-stained ventral horns (dashed lines) from vehicle (A,B) and compound 1 (C,D)-treated rats, as indicated; and E graphically depicts the area of WFA staining (as area per area of interest) calculated for each vehicle and compound 1-treated rats (scale bar=500 μm; * signifies statistically significant difference between groups; n=5 per group, unpaired t-test two tail p=0.0135);

FIG. 5 graphically depicts improvement of locomotor recovery after SCI from intrathecal administration of compound 1; where rats received a thoracic SCI and at the same time were implanted with an intrathecal pump to deliver either vehicle (open squares) or the SOX9 inhibitory compound 1 (closed squares) at the lumbar enlargement, over a period of 4 weeks; and where the treated rats showed improved hind limb function compared to controls (n=6 per group, 2-way repeated measures ANOVA p=0.03);

FIG. 6 graphically illustrates that compound 1 can penetrate the blood-spinal cord barrier, by showing the results when compound 1 (10 nmol/g) was intravenously injected into control or spinal cord injured rats 24 and 48 hours post-SCI; at three days post SCI 5 mm segments of the cord at the lesion and lumbar enlargements were harvested and analyzed fro compound 1 by ultra performance liquid chromatography coupled to mass spectrometry (the height of the peaks indicated relative concentrations of compound 1 at the lesion (black), distal to the lesion (grey) and in the uninjured spinal cord (dark grey));

FIGS. 7-10 graphically depict results of a bioassay to detect SOX9 inhibition by compounds according to specific embodiments of the present application (* significantly different from control by one-way ANOVA, Dunnett's multiple comparison test, P, 0.05);

FIG. 11 graphically depicts Acan expression in ATDC % cells treated with inhibitor compounds according to specific embodiments of the present application (* significantly different from control by one-way ANOVA, Dunnett's multiple comparison test, P, 0.05); and FIG. 12 graphically depicts Col1a2 expression in LX-2 cells serum-starved in 2% FBS and treated with 5 ng/mL TGFβ1 for 24 h in the presence of inhibitor compounds according to specific embodiments of the present application (* significantly different from control by one-way ANOVA, Dunnett's multiple comparison test, P, 0.05).

DETAILED DESCRIPTION

Definitions

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

As used herein, the term "alkyl" refers to a hydrocarbon radical derived from an alkane by removal of a hydrogen atom, and includes both branched and straight hydrocarbon radicals. In certain embodiments, the alkyl is a $C_1$ to $C_6$ alkyl, which may refer to the following groups: methyl, ethyl, n-propyl, isopropyl, cyclopropyl, n-butyl, isobutyl, sec-butyl, t-butyl, cyclobutyl, 2-methylbutyl, n-hexyl, and cyclohexyl.

As used herein, the term "heterocyclyl" refers to a 3 to 24-membered, or 3 to 10 membered, or 3 to 6 membered, cyclic radical that has atoms of at least two different elements as members of its ring(s), including carbon and at least one heteroatom. A heterocyclic substituent can be monocyclic or polycyclic. Heteroatoms are selected from oxygen, phosphorous, nitrogen, or sulfur. In certain embodiments, a heterocyclyl group is a 3 to 6 membered cyclic radical that contains oxygen, nitrogen or both. Examples of heterocyclyls include, but are not limited to, pyrrolidinyl, pyranyl, piperidinyl, morpholinyl, and piperazinyl.

As used herein, the term "halo" or "halogen," alone or in combination, refers to fluorine, chlorine, bromine, or iodine radicals.

The term "amino acid" refers to naturally occurring and non-naturally occurring amino acids, as well as amino acid analogs and amino acid mimetics that possess similar structural, chemical and/or functional characteristics to the naturally occurring amino acids.

Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Reference to an amino acid includes, for example, naturally occurring proteogenic L-amino acids as well as D-amino acids. Standard single letter or three letter notations have been used as follows:

A—Ala—alanine
C—Cys—cysteine
D—Asp—aspartic acid
E—Glu—glutamic acid
F—Phe—phenylalanine
G—Gly—glycine
H—His—histidine
I—Ile—Isoleucine
K—Lys—lysine
L—Leu—leucine
M—Met—methionine
N—Asn—asparagine
O—Pyl—pyrrolysine
P—Pro—proline
Q—Gln—glutamine
R—Arg—arginine
S—Ser—serine
T—Thr—threonine
U—Sec—selenocysteine
V—Val—valine
W—Trp—tryptophan
Y—Tyr—tyrosine.

The expression "amino acid analogs" as used herein, including in reference to non-naturally occurring amino acids and to modified naturally occurring amino acids, refers to compounds that have the same basic chemical structure as a naturally occurring amino acid, i.e., a carbon that is bound to a hydrogen, a carboxyl group, an amino group, and an R group, and includes, for example, homoserine, norleucine, methionine sulfoxide and methionine methyl sulfonium. Such analogs have modified R groups (such as, norleucine) or modified peptide backbones, but retain the same basic chemical structure as a naturally occurring amino acid. Amino acid analogs include chemically modified amino acids such as amino acid variants and derivatives; naturally occurring non-proteogenic amino acids such as β-alanine, ornithine, etc.; and chemically synthesized compounds having properties known in the art to be characteristic of amino acids. Examples of non-naturally occurring amino acids include, but are not limited to, α-methyl amino acids (e.g., α-methyl alanine), D-amino acids, histidine-like amino acids (e.g., 2-amino-histidine, β-hydroxy-histidine, homohistidine, α-fluoromethyl-histidine and α-methyl-histidine), amino acids having an extra methylene in the side chain ("homo" amino acids), and amino acids in which a carboxylic acid functional group in the side chain is replaced with a sulfonic acid group (e.g., cysteic acid). The incorporation of amino acid analogs, such as non-natural amino acids, including synthetic non-native amino acids or substituted amino acids, may be advantageous in a number of different ways.

The terms "polypeptide," "peptide" and "protein" refer to a polymer or oligomer of amino acid residues. The terms apply to naturally occurring amino acid polymers as well as amino acid polymers in which one or more amino acid residues are a non-naturally encoded amino acid. As used herein, the terms encompass amino acid chains of any length, including full length proteins, wherein the amino acid residues are linked by covalent peptide bonds. The polypeptides, peptides and proteins are written using standard sequence notation, with the nitrogen terminus being on the left and the carboxy terminus on the right.

The term "conservative amino acid substitutions" refers to all substitutions wherein the substituted amino acid has similar structural, chemical and/or functional properties with the corresponding amino acid in the reference sequence. By way of example, conservative amino acid substitutions involve substitution of one aliphatic or hydrophobic amino acid, e.g., alanine, valine, leucine, isoleucine, methionine, phenylalanine, or tryptophan with another; substitution of one hydroxyl-containing amino acid, e.g., serine and threonine, with another; substitution of one acidic residue, e.g., glutamic acid or aspartic acid, with another; replacement of one amide-containing residue, e.g., asparagine and glutamine, with another; replacement of one aromatic residue, e.g., phenylalanine and tyrosine, with another; replacement of one basic residue, e.g., lysine, arginine and histidine, with another; and replacement of one small amino acid, e.g., alanine, serine, threonine, and glycine, with another. Conservative substitution tables providing functionally similar amino acids are known to those of ordinary skill in the art. Peptides comprising one or more conservative amino acid substitution are referred to herein as "conservative variants".

As used herein, "pharmaceutically acceptable" means approved or approvable by a regulatory agency of a federal or a state/provincial government or the corresponding agency in countries other than the United States or Canada, or that is listed in the U.S. Pharmacopoeia or other generally recognized pharmacopoeia for use in animals, including in humans.

As used herein, the term "subject" refers to a human or a non-human animal (e.g., a mammal) that is need of treatment, or potentially in need of treatment, as described herein.

As used herein, the term "in need thereof" is used to refer to a judgment made by a physician or other caregiver (e.g., a veterinarian) that a subject requires or will benefit from treatment or preventative care. This judgment is made based on a variety of factors that are in the realm of the physician's or caregiver's expertise.

As used herein, the term "effective amount" as used in respect of a particular result to be achieved is an amount sufficient to achieve the desired result. For example, an "effective amount" of drug when referred to in respect of cancer treatment, refers to an amount of drug sufficient to reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; increase survival time; and/or relieve to some extent one or more of the symptoms associated with the cancer.

The present application provides compounds useful as inhibitors of SOX9 activity, and compositions comprising the SOX9 inhibitor compounds, and uses thereof in the treatment of a disease or condition characterized by over activity of SOX9 and/or over expression of CSPGs or a disease or condition that may be ameliorated by SOX9 inhibition or by decreased CSPG levels.

SOX9 has been identified as a transcription factor that up-regulates the expression of the enzymes XT-I, XT-II and C4ST in reactive astrocytes (Gris et al 2007). This suggested that SOX9 inhibition after CNS injury could lead to decreased CSPG levels, a lesion microenvironment that promotes axonal sprouting and better neurological recovery. SOX9 loss of function studies after SCI were carried out using a mouse model prepared from two mouse strains. The first carries floxed SOX9 alleles (Stolt et al 2003 and Akiyama et al 2002) (exons 2 and 3 of SOX9 surrounded by loxP sites). The second is a transgenic line that ubiquitously expresses a tamoxifen-inducible Cre recombinase (Hayashi & McMahon 2002). By breeding the $SOX9^{flox/flox}$ mice to the CAGGCre-ER mice offspring were generated ($SOX9^{flox/flox}$; CAGGCre-ER) in which tamoxifen administration, followed by SCI permitted the molecular, cellular and neurological responses to SCI in the presence of greatly reduced levels of SOX9. These tamoxifen-inducible conditional SOX9 knock out mice demonstrated that:

- SOX9 conditional knockouts had reduced CSPG levels compared to controls after SCI (McKillop et al 2013);
- SOX9 conditional knockouts had improved locomotor recovery after SCI (McKillop et al 2013);
- The improved locomotor recovery in spinal cord-injured SOX9 conditional knockout mice was due to reparative sprouting and dependent on the reduction of CSPG levels (McKillop et al 2016); and
- SOX9 conditional knockouts had reduced CSPG levels, increased reparative sprouting and improved recovery after stroke (Xu et al 2018).

These studies demonstrate that SOX9 knockout mice have improved recovery after CNS injury because of reduced CSPG levels in the PNN surrounding neurons that have been denervated by injury.

Furthermore, as a regulator of extracellular matrix gene expression, SOX9 is also implicated in fibrotic diseases. Recently it has been shown that SOX9 levels in liver biopsies from patients with chronic liver disease correlates with the severity of fibrosis and can be used to predict progression to cirrhosis (Athwal et al 2017). A SOX9 conditional knockout was used to show that SOX9 ablation protected mice against parenchymal and biliary fibrosis, improved liver function and reduced inflammation (Athwal et al 2017).

Driving SOX9 expression in human chondrocytes increases their production of proteoglycans and collagen (Rey-Rico et al 2018 and Cucchiarini et al 2007), demonstrating that SOX9 regulates matrix production in humans as in rodents. Furthermore, SOX9 levels in biopsies from patients with chronic liver disease correlate to levels of fibrosis and can predict disease progression to cirrhosis (Athwal et al 2017). Also, SOX9 levels are greatly increased in pathology samples from human subjects after stroke, traumatic brain injury (TBI) and SCI (FIG. 1).

SOX9 has also been implicated in cancer development and progression. For example, SOX9 is overexpressed in cancers such as glioblastoma (Hiraoka et al 2015) and prostate cancer (Francis et al 2018). SOX9 has also been shown to be a key regulator in various processes during embryogenesis, stem cell commitment and cancer. Furthermore, SOX 9 activity has been shown to increase resistance to cancer therapeutics, for example, for the treatment of estrogen receptor positive breast cancer (Voronkova et al 2019) and lung cancer (Francis et al 2018).

Accordingly, the present inventors sought to develop inhibitors of SOX9 useful in the treatment of diseases and disorders characterized by increased SOX9 activity and/or increase CSPG expression. Such inhibitor compounds are useful in the treatment of, for example, stroke, TBI and SCI, liver disease and cancer.

SOX9 Inhibitor Compounds

The present application provides SOX9 inhibitor compounds that act to reduce SOX9 expression and/or SOX9 activity. The SOX9 inhibitor compounds are small molecules or peptides.

In one aspect of the present application there is provided a small molecule SOX9 inhibitor compound of formula I

I

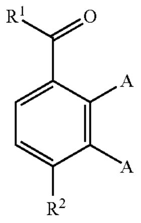

where:

$R^1$ is $NR^7R^8$, wherein $R^7$ and $R^8$ are each independently a straight or branched $C_1$ to $C_6$ alkyl, or $R^7$ and $R^8$, together with the N atom to which they are attached, form a substituted or unsubstituted heterocyclyl containing one or two heteroatoms selected from N and O;

$R^2$ is H, a $C_1$ to $C_6$ alkyl, a $C_1$ to $C_6$ alkoxy, or halo; and one A is H and the other is:

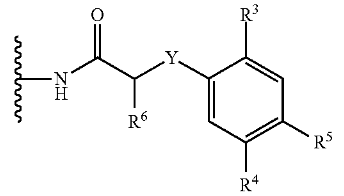

where:

$R^3$ is H or a $C_2$ to $C_6$ alkyl;

$R^4$ is H or a $C_1$ to $C_6$ alkyl;

$R^5$ is H, halo or $NCH_2C_6H_5$;

$R^6$ is H or methyl; and

Y is O or $SO_2$.

In accordance with certain embodiments, $R^1$ is piperazine, N-methylpiperazine, morpholine, piperidine, pyrrolidine or $N(C_1$-$C_6$ alkyl$)_2$.

In accordance with certain embodiments, $R^1$, $R^3$, $R^4$, $R^5$, $R^6$, A and Y are as defined above, including any specific embodiments thereof, and $R^2$ is H, methyl, methoxy or Cl.

In accordance with certain embodiments $R^1$, $R^2$, $R^4$, $R^5$, $R^6$, A and Y are as defined above, including any specific embodiments thereof, and $R^3$ is H or isopropyl.

In accordance with certain embodiments $R^1$, $R^2$, $R^3$, $R^5$, $R^6$, A and Y are as defined above, including any specific embodiments thereof, and $R^4$ is H or methyl.

In accordance with certain embodiments $R^1$, $R^2$, $R^3$, $R^4$, $R^6$, A and Y are as defined above, including any specific embodiments thereof, and $R^5$ is H, Cl or $NCH_2C_6H_5$.

In accordance with certain embodiments $R^1$, $R^2$, $R^3$, $R^4$, $R^5$, A and Y are as defined above, including any specific embodiments thereof, and $R^6$ is H.

In accordance with certain embodiments $R^1$, $R^2$, $R^3$, $R^4$, $R^5$, $R^6$ and A are as defined above, including any specific embodiments thereof, and Y is O.

In accordance with further embodiments, $R^1$, $R^2$, $R^3$, $R^4$, $R^5$, $R^6$ and Y are as defined above, including any specific embodiments thereof, and the A in the ortho position relative to $R^1$ is H.

In certain embodiments, the SOX9 inhibitor compound of the present application is not:

1

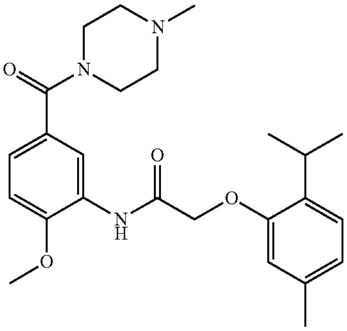

or

-continued

2

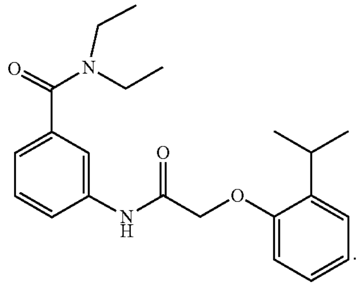

Non-limiting examples of SOX9 inhibitor compounds useful in the compositions and methods of the present application are depicted below:

1

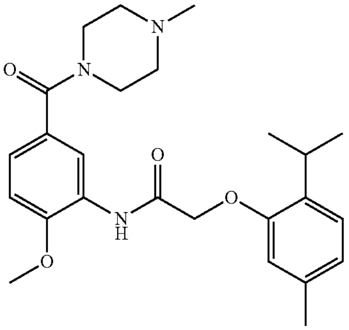

767

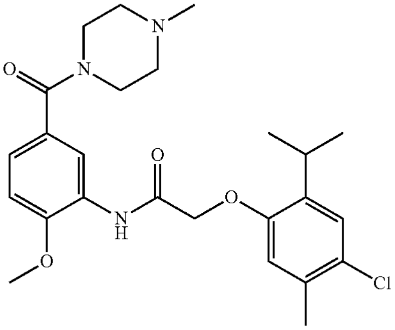

756

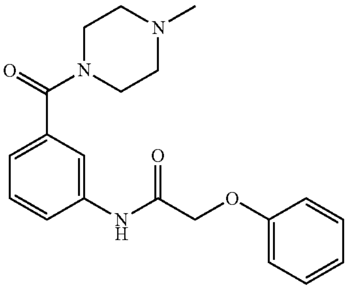

-continued
757
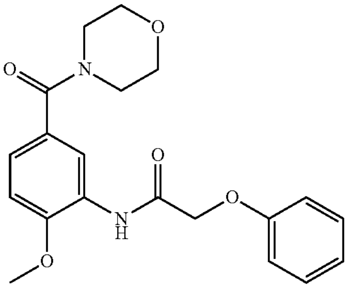
758
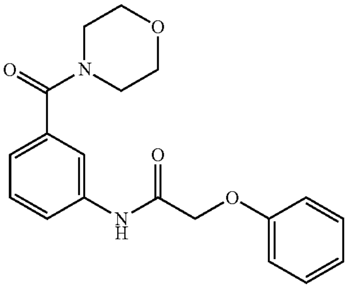
760
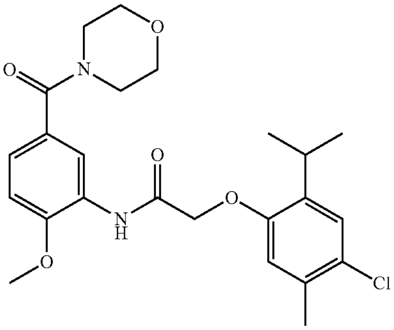
765
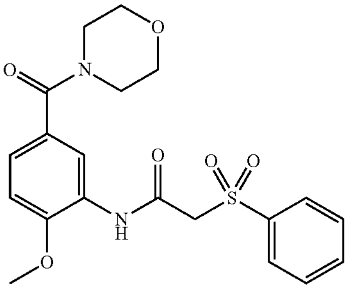
782
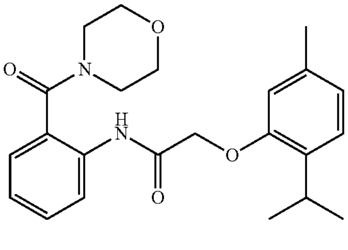
-continued
751
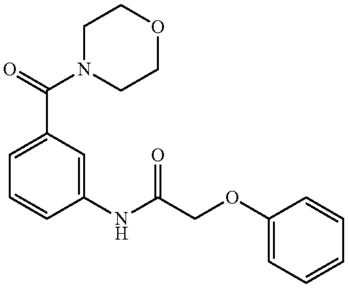
752
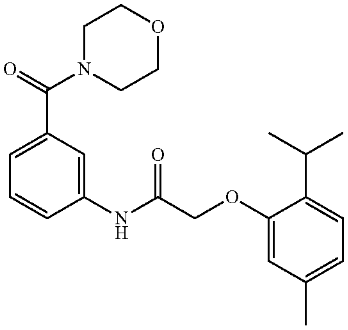
754
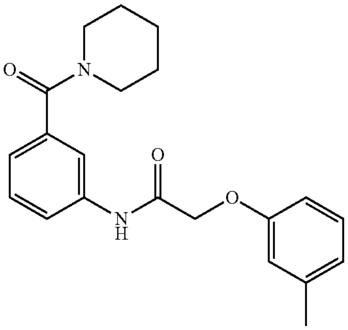
755
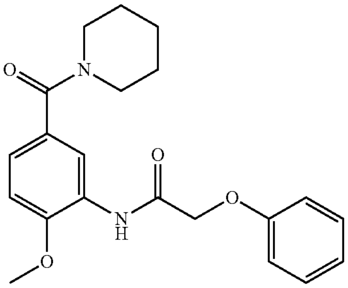
768
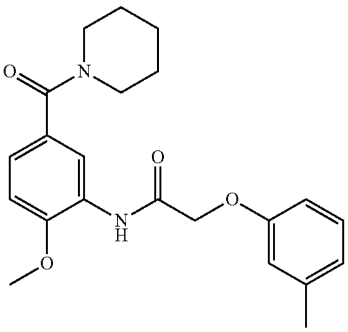

-continued
759
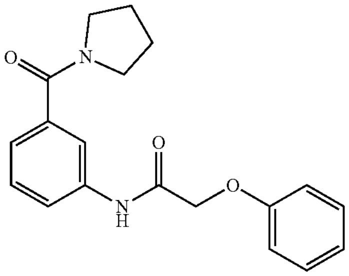
781
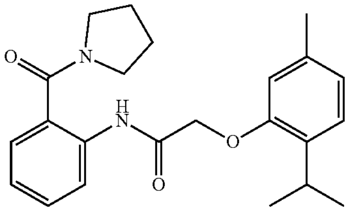
761
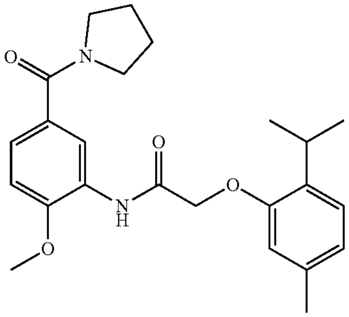
790
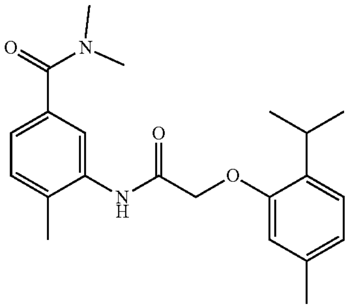
2
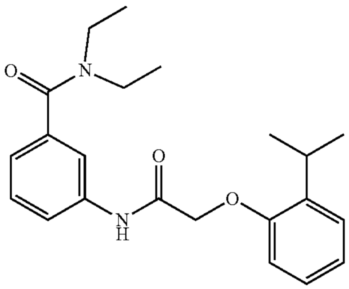
-continued
787
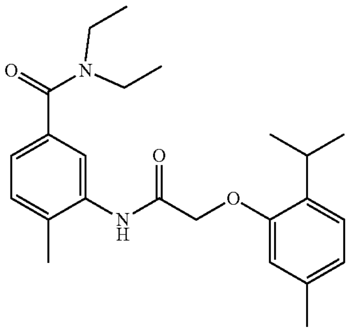
815
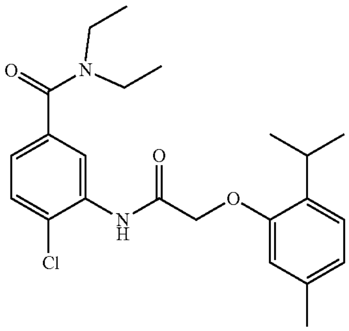
817
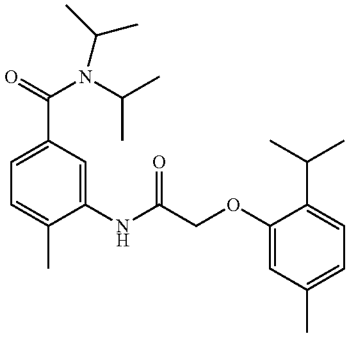
835
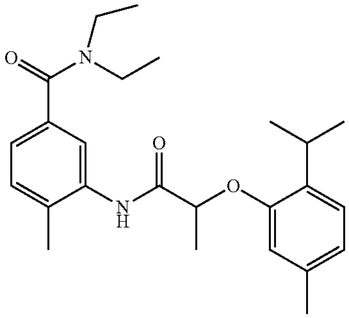

-continued

844

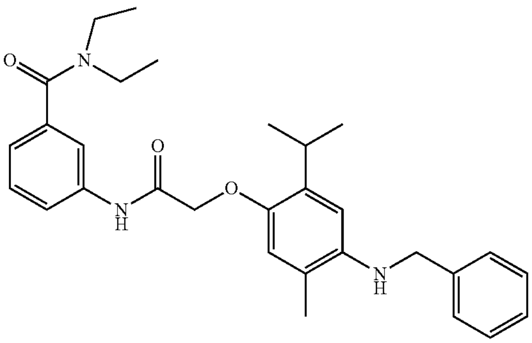

838

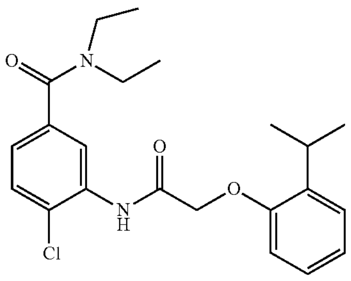

822

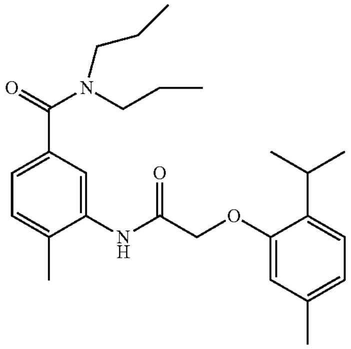

816

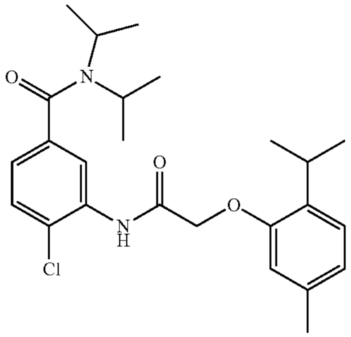

The inhibitor compounds of the present application can be neutral or can carry a positive or negative charge. Where the compound is positively or negatively charged, the compound can exist as a pharmaceutically acceptable salt, which includes both acid and base addition salts.

Pharmaceutically acceptable acid addition salts are those salts that retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid, and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

Pharmaceutically acceptable base addition salts are those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts, and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2 dimethylaminoethanol, 2 diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins, and the like. Particularly preferred organic bases are isopropylamine, diethylamine, ethanolamine, trimethylamine, dicyclohexylamine, choline and caffeine.

Accordingly, the present application further provides pharmaceutically acceptable salts of the compound of formula I.

Often crystallizations produce a solvate of the compound described herein. As used herein, the term "solvate" refers to an aggregate that comprises one or more molecules of a compound described herein with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate, and the like, as well as the corresponding solvated forms. The compound described herein may be true solvates, while in other cases, the compound described herein may merely retain adventitious water or organic solvent or be a mixture of water plus some adventitious solvent.

Accordingly, the present application further provides pharmaceutically acceptable solvates of the compound of formula I or salts thereof.

Another aspect of the present application provides a SOX9 inhibitor compound that is a peptide comprising at least a portion of the SOX9 dimerization motif. In one embodiment, the inhibitor peptide comprises the sequence of SEQ ID NO: 1 (IREAVSQ). In one embodiment, the peptide SOX9 inhibitor compound comprises the sequence of SEQ ID NO: 2 (DKFPVCIREAVSQVLKGYDW). This sequence corresponds to a portion of the SOX9 dimerization motif that is 100% conserved between mice, rats and humans.

The peptides disclosed herein can include peptides comprising an amino acid sequence having at least 80%, at least 85%, at least 90%, at least 95%, at least 96%, at least 97%, at least 98%, at least 99% of sequence identity with the peptide of SEQ ID NO:1. In accordance with one embodiment, the inhibitory peptide comprises one or more amino acid analogue. Examples of different amino analogues that can be included in the peptides and methods and compositions of the present application are described above. The amino acid subunits are, in certain embodiments, linked by peptide bonds. In other embodiments, two or more amino acid subunits are linked by another type of bond, e.g. ester, ether, etc. In certain embodiments, peptidomimetics or amino acid analogues are incorporated into the peptide in order to reduce or eliminate proteolytic enzyme or protease susceptibility and improve stability of the peptide in vivo. In an alternative embodiment, the peptide is cyclized (between side chains or the termini of the peptide), again to reduce susceptibility to proteolytic enzymes or proteases and to improve stability. The incorporation of peptidomimetics or amino acid analogues, and/or the cyclization of the peptide is performed such that it does not reduce or significantly reduce the inhibitory effect of the peptide.

The peptides disclosed herein can be produced using conventional methods of peptide synthesis. Alternatively, the peptides can be produced using conventional methods of recombinant technology using nucleic acids that can express the inhibitory peptides from appropriate vectors and host cells, as are well known to workers skilled in the art.

Optionally the inhibitory peptide is beneficially modified by methods known to enhance passage of the molecule across cellular membranes and/or across the blood-brain barrier. For example, in one embodiment the peptide additionally comprises a polypeptide portion that facilitates transport of the peptide across cellular membranes. For example, the inhibitory peptide can comprise a cell-penetrating peptide (CPP), protein transduction domain (PTD), spontaneous membrane translocating peptide (SMTP) or the like. Examples of such peptide sequences are well known to those of skill in the art and selection of the appropriate sequence can be made readily based on various factors, such as, for example, target tissue or cell type, type of subject, delivery composition and overall length of the inhibitory peptide.

Examples of sequences and transporters that are useful in facilitating transport of the peptide across cellular membranes are Antennapedia sequences, TAT, HIV-TAT, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol). These can be included as part of the inhibitory peptide, or can be formulated for administration together with the inhibitory peptide.

In one embodiment, the inhibitory peptide has the sequence DKFPVCIREAVSQVLKGYDWKYGRKKRR-QRRR (SEQ ID NO:3), which includes a portion of the SOX9 dimerization motif (SEQ ID NO:2) and an HIV TAT sequence.

Synthesis of Small Molecule SOX9 Inhibitor Compounds

The small molecule inhibitor compounds of the present application can be considered to consist of four distinct units (A, B, C and D) as shown in the exemplary retrosynthetic scheme 1 below. These compounds can be generated in a 4-step process.

The first step comprises combining unit A (e.g., a 1,4 piperazine unit) with an acid chloride derived from a nitrobenzoic acid unit B. In step 2 the aromatic nitro group from step 1 is reduced to an amino group. In step 3 the CD moiety is prepared by reacting the phenol unit D with chloroacetic acid C in the presence of excess base, e.g., sodium carbonate. In step 4 the acetic acid from step 3 is converted to its acid chloride (for example, with thionyl chloride) and then coupled with amine AB. Analogs are generated by changing one or more of the A-D units, for example by adding substituents.

Scheme 1

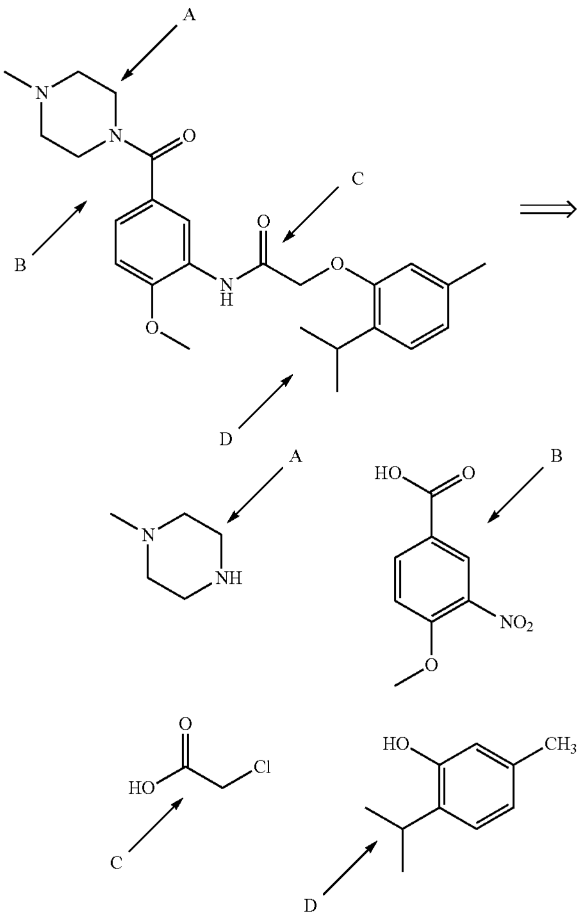

Therapeutic Use of SOX9 Inhibitor Compounds

The present application further provides use of the herein described inhibitors of SOX9 in the treatment or prevention of diseases and disorders characterized by increased SOX9 activity and/or increased CSPG expression or a disease or disorder that may be ameliorated by decreasing SOX9 or CSPG levels. The disease or disorder can be, for example, a condition involving inhibited neuronal growth or neuronal plasticity (such as stroke, TBI or SCI), fibrotic disorders (e.g., liver fibrosis) and cancer.

Reducing SOX9 activity, for example in an injured nervous system, can lead to reduced chondroitin sulfate proteoglycan (CSPG) levels (McKillop 2013). Reduced CSPG levels can thereby promote reparative nerve growth. Reparative nerve growth is the natural process by which the nervous system recovers from injury or disease. Thus, the inhibition of SOX9 can potentiate and/or amplify this normal mechanism of repair. Therefore, the SOX9 inhibitor compounds and compositions of the present application are useful for treating a condition associated with proteoglycan, particularly a chondroitin sulfate proteoglycan, production or modulation in a subject.

Accordingly, the present application provides a method of treating a disease or condition associated with increased SOX9 activity and/or increased CSPG expression, or a disease or disorder that may be ameliorated by decreasing SOX9 or CSPG levels, comprising administering to a subject in need thereof a therapeutically effective amount of a SOX 9 inhibitor that is:

(i) a peptide comprising a sequence having at least 80% sequence identity with the peptide of SEQ ID NO:1; or (ii) a compound of formula I:

I

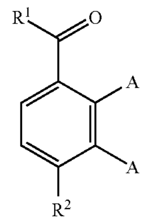

where:

$R^1$ is $NR^7R^8$, wherein $R^7$ and $R^8$ are each independently a straight or branched $C_1$ to $C_6$ alkyl, or $R^7$ and $R^8$, together with the N atom to which they are attached, form a substituted or unsubstituted heterocyclyl containing one or two heteroatoms selected from N and O;

$R^2$ is H, a $C_1$ to $C_6$ alkyl, a $C_1$ to $C_6$ alkoxy, or halo; and one A is H and the other is:

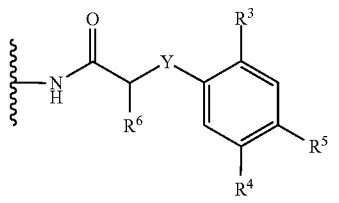

where:

$R^3$ is H or a $C_2$ to $C_6$ alkyl;

$R^4$ is H or a $C_1$ to $C_6$ alkyl;

$R^5$ is H, halo or $NCH_2C_6H_5$;

$R^6$ is H or methyl; and

Y is O or $SO_2$.

In certain embodiments, the disease or condition is a condition involving inhibited neuronal growth or neuronal plasticity. Inhibitor compounds of the present application can be used to treat nerve damage, especially damage to the central nervous system (CNS). The treatment can be applicable to new and/or old injuries as the treatment augments neuroplasticity, which can be therapeutically beneficial at any time after injury. Examples of conditions that may be treated include, but are not limited to, primary conditions of the nervous system that include but are not limited to, spinal cord injury, traumatic brain injury, neurodegenerative diseases (e.g., Friedreich's ataxia, spinocerebellar ataxia, Alzheimer's disease, Parkinson's Disease, Lou Gehrig's Disease (ALS)), demyelinative diseases (e.g. multiple sclerosis, transverse myelitis resulting from spinal cord injury, inflammation), diseases associated with retinal neuronal degeneration (e.g., age-related amblyopia, maculopathies and retinopathies such as viral, toxic, diabetic and ischemic, inherited retinal degeneration such as Kjellin and Barnard-Scholz syndromes, degenerative myopia, acute retinal necrosis) and age-related pathologies such as loss of cognitive function. Examples also include conditions that cause cerebrovascular injury including, but not limited to, stroke, vascular malformations (e.g., arteriovenous malformation (AVM), dural arteriovenous fistula (AVF), spinal hemangioma. cavernous angioma and aneurysm), ischemia resulting from occlusion of spinal blood vessels, including dissecting aortic aneurisms, emboli, arteriosclerosis and developmental disorders, (e.g. spina bifida and meningomyolcoele). The compounds are particularly useful for treating central nervous system damage caused by spinal cord injury, stroke or traumatic brain injury.

In accordance with certain embodiments, there is provided a method of treating disease or condition is a condition involving inhibition of neuronal growth or neuronal plasticity, such as SCI, in which the compound of formula I is not

1

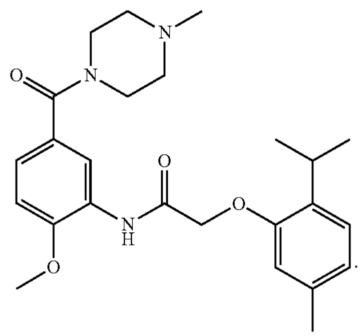

In other embodiments the SOX9 inhibitor compound of the present application is useful for the treatment of liver disease, such as but not limited to non-alcoholic fatty liver disease, liver fibrosis, such as parenchymal and biliary fibrosis. The SOX9 inhibitor compound can act to improve liver function and/or reduce inflammation. Accordingly, the present application further provides a method for the treatment or prevention of fibrotic disease comprising administering to a subject in need thereof a therapeutically effective amount of a SOX 9 inhibitor that is:

(i) a peptide comprising a sequence having at least 80% sequence identity with the peptide of SEQ ID NO:1; or (ii) a compound of formula I:

I

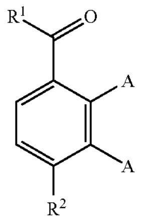

where:

$R^1$ is $NR^7R^8$, wherein $R^7$ and $R^8$ are each independently a straight or branched $C_1$ to $C_6$ alkyl, or $R^7$ and $R^8$, together with the N atom to which they are attached, form a substituted or unsubstituted heterocyclyl containing one or two heteroatoms selected from N and O;

$R^2$ is H, a $C_1$ to $C_6$ alkyl, a $C_1$ to $C_6$ alkoxy, or halo; and one A is H and the other is:

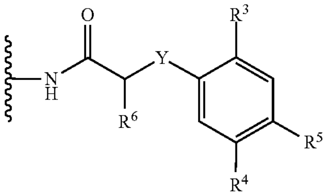

where:

$R^3$ is H or a $C_2$ to $C_6$ alkyl;

$R^4$ is H or a $C_1$ to $C_6$ alkyl;

$R^5$ is H, halo or $NCH_2C_6H_5$;

$R^6$ is H or methyl; and

Y is O or $SO_2$.

In other embodiments, the SOX9 inhibitor compounds of the present application are useful for the treatment of a cancer in which SOX9 is overexpressed (e.g., glioblastoma (Hiraoka et al 2015) and prostate cancer (Francis et al 2018). SOX9 has been shown to be a key regulator in various processes during embryogenesis, stem cell commitment and cancer.

In other embodiments, the SOX9 inhibitor compounds of the present application are useful in the treatment of cancer in which SOX9 activity causes resistance to therapy. For example, tamoxifen resistance in estrogen receptor positive breast cancer can be caused by SOX9 (Xue et al 2019). Also SOX9 expression has been found to be elevated following cisplatin treatment of lung cancer patients, and that this overexpression correlates with worse survival (Voronkova et al 2019). Further SOX9 expression induces chemoresistance while knock down of SOX9 expression increases cellular sensitivity to cisplatin (Voronkova et al 2019).

Accordingly, the present application further provides a method for the treatment or prevention of cancer comprising administering to a subject in need thereof a therapeutically effective amount of a SOX 9 inhibitor that is:

(i) a peptide comprising a sequence having at least 80% sequence identity with the peptide of SEQ ID NO:1; or (ii) a compound of formula I:

I

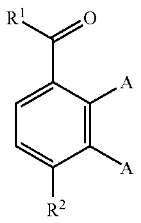

where:

$R^1$ is $NR^7R^8$, wherein $R^7$ and $R^8$ are each independently a straight or branched $C_1$ to $C_6$ alkyl, or $R^7$ and $R^8$, together with the N atom to which they are attached, form a substituted or unsubstituted heterocyclyl containing one or two heteroatoms selected from N and O;

$R^2$ is H, a $C_1$ to $C_6$ alkyl, a $C_1$ to $C_6$ alkoxy, or halo; and one A is H and the other is:

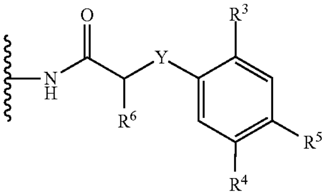

where:

$R^3$ is H or a $C_2$ to $C_6$ alkyl;

$R^4$ is H or a $C_1$ to $C_6$ alkyl;

$R^5$ is H, halo or $NCH_2C_6H_5$;

$R^6$ is H or methyl; and

Y is O or $SO_2$.

In certain embodiments of this method, the SOX9 inhibitor compound is administered in combination with another chemotherapeutic. This is particularly beneficial in cases where SOX9 activity induces resistance to the chemotherapeutic and the SOX9 inhibitor compound then causes an increased sensitive to the chemotherapeutic. The SOX9 inhibitor compound can be administered prior to, simultaneously with or after administration of the other chemotherapeutic.

Pharmaceutical Compositions

For the purposes of administration, the compounds of the present disclosure may be administered as a raw chemical or may be formulated as pharmaceutical compositions. Accordingly, the present application further provides pharmaceutical compositions comprising a SOX9 inhibitor compound as described herein, or a combination of SOX9 inhibitor compounds as described herein.

The pharmaceutical compositions of the present application can be prepared by combining a SOX9 inhibitor compound described herein with an appropriate pharmaceutically acceptable carrier, diluent or excipient, and may be formulated into preparations in solid, semi solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the present application are formulated so as to allow the active ingredients contained therein to be bioavailable upon administration of the composition to a subject. Compositions that will be administered to a subject take the form of one or more dosage units, where for example, a tablet may be a single dosage unit, and a container of a SOX9 inhibitor compound described herein in aerosol form may hold a plurality of dosage units. Actual methods of preparing such dosage forms are known, or will be apparent, to those skilled in this art; for example, see Remington: The Science and Practice of Pharmacy (22nd ed.) eds. Loyd V. Allen, Jr., et al., Pharmaceutical Press, 2012. The composition to be administered will, in any event, contain a therapeutically effective amount of a compound described herein, or a pharmaceutically acceptable salt or solvate thereof, for treatment of a disease or condition of interest in accordance with the teachings of this disclosure.

To gain a better understanding of the invention described herein, the following examples are set forth. It should be understood that these examples are for illustrative purposes only. Therefore, they should not limit the scope of this invention in any way.

EXAMPLES

Example 1: Peptide Inhibitor of SOX9

SOX9 is a member of the SRY-related, high mobility group box (Sox) transcription factors. SOX9 mutations cause campomelic dysplasia a disorder characterized by skeletal malformations, sex reversal and mental retardation (Wagner et al 1994). The abnormalities caused by SOX9 mutations corresponds to its well-known roles in chondrogenesis, testes differentiation and nervous system development. An investigation of a campomelic dysplasia patient who had skeletal abnormalities but not sex reversal revealed that they harboured a mutation in the SOX9 dimerization domain (Bernard et al 2003). This work led to the demonstration that SOX9-driven transcription of extracellular matrix (ECM) genes (such as collagen genes and aggrecan) requires dimerization whereas SOX9-driven transcription of sex determination genes (such as steroidogenic factor 1, SF1) does not require SOX9 dimerization (Bernard et al 2003, Sock et al 2003 and Coustry et al 2010). Sequence analyses from the promoter regions of SOX9-responsive genes revealed that ECM genes dependent on SOX9 dimerization for transcriptional activation have two SOX9 binding sites whereas the promoters of sex determination genes not requiring SOX9 dimerization only have one SOX9 binding site (Sock et al 2003).

In an attempt to demonstrate the dependence of ECM gene transcription on SOX9 dimerization a novel peptide (SOX-DIMER) was synthesized to block SOX9 dimerization specifically. This peptide is a fusion between the SOX9 dimerization motif (DKFPVCIREAVSQVLKGYDW (SEQ ID NO. 2)) and the protein transduction domain of the HIV-1 Tat protein (Schwarze et al 1999). The Tat sequence in this peptide serves to ensure the peptide's entry into cells.

Primary astrocyte cultures were treated with 10 μM SOX-DIMER peptide or of a control peptide (FLAG-Tat) for 48 h and then harvested RNA. Using Quantitative-PCR (Q-PCR) it was found that SOX-DIMER functioned successfully as a SOX9 inhibitor compound by significantly reducing the expression of SOX9 and SOX9 target genes including: 1) the chondroitin sulfate synthesizing enzymes XT-1 and XT-2, 2) link protein (Hapln1, links CSPGs to hyaluronic acid in the extracellular matrix), 3) Collagen 2a1, 4) GFAP and 5) the CSPG core proteins aggrecan and brevican (FIG. 2).

Example 2: Small Molecule Inhibitor of SOX9

To identify small molecule inhibitors of SOX9 design efforts focused on the septameric peptide sequence (IREAVSQ, SEQ ID NO:1, underlined in the SOX-DIMER sequence given above) identified as a subregion of the known SOX9 dimerization domain with a high likelihood of direct participation in dimerization. This prediction was based on the position of the human mutation that causes the skeletal but not the sex reversal abnormalities of campomelic dyskplasia (Bernard et al 2003). A computational screen of ~12 million compounds was performed to identify small molecules predicted to interfere with SOX9 dimerization, based on the physical-chemical properties of the SOX-DIMER peptide motif. Compound 1, shown below, was identified by the screen and then experimentally found to decrease SOX9 target gene expression in primary mouse and rat astrocyte cultures and in the chondrogenic cell line ATDC5 (FIG. 3).

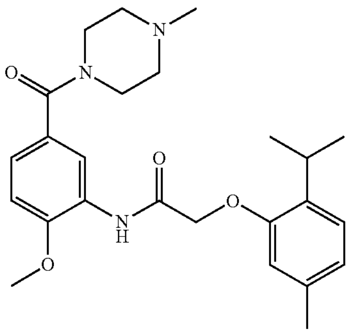

1

To assess the effect of compound 1 on CSPG levels in the injured rat spinal cord, compound 1 or vehicle was delivered by an intrathecal pump delivering compound 1 at approximately 400 μg/Kg/day for 4 weeks starting immediately after a 200 kdyne T9 thoracic SCI. This dose was predicted to result in a concentration of compound 1 of between 10 and 30 μM based on an estimated cerebrospinal fluid volume of 580 μL (Murtha et al 2014) and a turnover rate of about 12-13 times per day (Simon et al 1995). Histological sections caudal to the lesion in these rats showed a 3-fold reduction in CSPG levels in rats treated with compound 1, as assessed by biotinytlated-WFA staining (FIG. 4) quantified using ImagePro™ software as previously described (McKillop et al 2013).

In a longer-term study, compound 1 (approximately 400 μg/Kg/day) or vehicle was again delivered intrathecally to rats immediately after a T9, 200 kdyne SCI, and hind limb function was evaluated twice per week by an observer blinded to treatment group in an open field test for 7 weeks (FIG. 5). These analyses showed a statistically significant improvement in the hind limb function of the compound 1-treated rats. By day 56 the compound 1-treated rats achieved average locomotor BBB scores (Basso et al 1995) of 12.4±0.8 indicating consistent weight supported plantar placement and occasional forelimb/hind limb coordination while the vehicle-treated rats only achieved an average locomotor BBB score of 10.4±0.7, indicating occasional weight supported planter placement with no forelimb/hind limb coordination.

It is anticipated that delaying the administration of the inhibitory compound until day 2 post-SCI will improve the therapeutic effects even more, as reducing CSPG levels by xyloside administration immediately after SCI has been shown to worsen outcomes compared to a 2 day delayed administration protocol (Rolls et al 2008).

Compound 1 was delivered intrathecally as it was initially unknown the inhibitory compound could cross the blood brain barrier. To resolve this issue a subsequent study was carried out in which control and T9 spinal cord injured rats were given intravenous injections of compound 1 (1 or 10 nmol/g) or of vehicle at 24 and 48 h after SCI and sacrificed 24 h later. Ultra performance liquid chromatography (UPLC), coupled to mass spectrometry, demonstrated significant levels of compound 1 at the lesion and distal to the lesion (in the lumbar enlargement). Compound 1 was even found in the spinal cords after dosing uninjured controls (FIG. 6).

Using a standard curve, the concentration of compound 1 in the injured spinal cord after a 10 nmol/g iv injection was determined to be 2.7 μM at the lesion epicenter, 1.9 μM in the lumbar cord and 1.02 μM in the uninjured cord. After the 1 nmol/g injections, concentrations of compound 1 were correspondingly reduced 10-fold. The significant levels of compound 1 found in uninjured rats indicated that damage to the blood spinal cord barrier due to SCI is not necessary for compound 1 to penetrate the CNS.

Example 3: Synthesis of Small Molecule Inhibitors of SOX9

Experimental

Reactions

All reactions were monitored by TLC using aluminum backed TLC plates (EMD Chemicals, TLC Silica Gel 60 F254), which were visualized by UV lamp (254 nm—fixed wavelength). Plates were then permanently stained with Hannessian's stain. All moisture sensitive reactions were carried out under nitrogen or argon atmosphere. Anhydrous THF was prepared by distillation from sodium and benzophenone and DCM from calcium hydride.

Purification

Purification by column chromatography was performed using SiliCycle SiliFlash® F60 silica gel of 230-400 mesh and glass columns fitted with a cotton piece and sand or fritted glass filter. Elutions were carried out with mixtures of hexanes and ethyl acetate.

NMR $^{1}H$ NMR and $^{11}C$ NMR were recorded on Bruker Avance™ 400 spectrometer.

Samples were dissolved in deuterated chloroform, methanol or acetone as indicated. All chemical shifts are reported in parts per million (ppm) and are referenced accordingly to the deuterated solvent used. Integrations are listed in parentheses along with coupling constants which are reported in Hz, where applicable.

General Procedures

General Procedure 1: Amide Synthesis

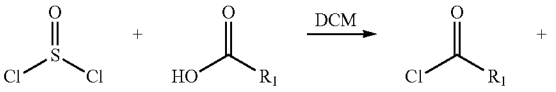

-continued

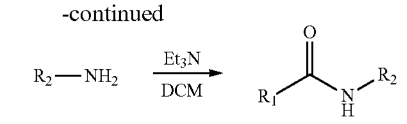

In a round bottom flask equipped with a magnetic stirrer, selected aryloxyacetic acid (1 equiv.) was dissolved in dichloromethane (DCM). Thionyl chloride (3 equiv.) was then added to the mixture and was refluxed under nitrogen atmosphere. The mixture was then refluxed for approximately 1 hour. In a different round bottom flask equipped with a magnetic stirrer, the selected amine (1.1 equiv.) was dissolved in DCM and left to stir. Triethyl amine (4 equiv.) was then added and the reaction was placed in an ice bath. After stirring for 10 minutes the corresponding acyl chloride (1 equiv.) was added slowly, dropwise. The solution was left to stir for approximately 1 hour, or until deemed complete by TLC analysis. Workup of the reaction involved quenching with distilled water followed by base (5% NaOH) and acid (5% HCl) washes for extraction of product from starting materials. The combined organic extracts were dried (MgSO4), filtered and concentrated in vacuo. The product was purified either by recrystallization or by column chromatography and the final compound was analyzed by NMR.

General Procedure #2: Nitro Group Reduction

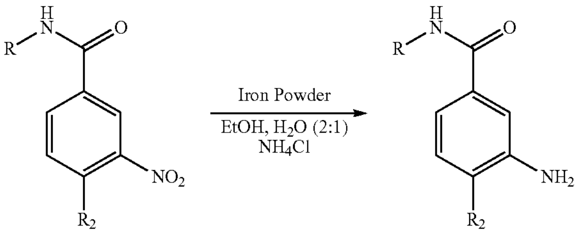

In a round bottom flask, the selected nitro-group compound (1 equiv.) was dissolved in a 2:1 mixture of ethanol (EtOH) and $H_2O$. Iron powder (5.5 equiv.) and ammonium chloride ($NH_4Cl$) (0.58 equiv.) were added. The mixture was refluxed for approximately 1 hour. Once deemed complete by TLC analysis, the mixture was filtered through Celite™ and extracted with DCM. The solution was dried with $MgSO_4$, which was then filtered off. The resulting solution was concentrated in vacuo and the product was purified either by recrystallization (ethyl acetate and hexanes) or column chromatography. The purified compound was analyzed by NMR.

General Procedure #3: Chloroacetic Acid Coupling

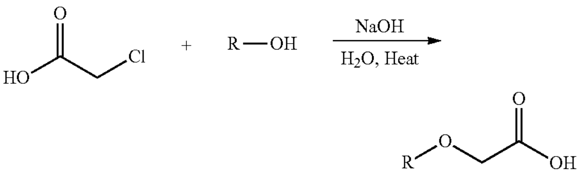

In a round bottom flask equipped with a magnetic stirrer, selected alcohol (1.1 equiv.) was dissolved in $dH_2O$ with chloroacetic acid (1 equiv.). Solid NaOH (3 equiv.) was then added to the flask and the reaction was brought to reflux. Once the reaction was deemed complete by TLC analysis, the mixture was cooled to room temperature and carefully acidified with concentrated HCl. The product was filtered off from the solvent and purified by recrystallization (Ethyl Acetate and Hexanes). The product was then characterized by NMR analysis.

General Procedure #4: Sulfide Oxidation

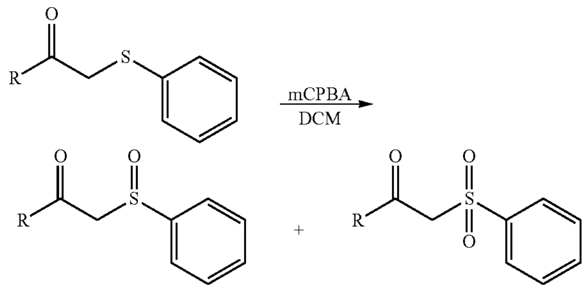

In a round bottom flask equipped with a magnetic stirrer, selected sulfide (1 equiv.) was dissolved in approximately 8 mL of DCM and left to stir for a couple minutes. mCPBA (2 equiv.) was then added and the reaction was left to stir until deemed complete by TLC analysis. Once complete, the products were extracted with 5% NaOH. The organic extracts were combined, dried ($MgSO_4$), filtered and evaporated in vacuo. The products were separated by column chromatography using a gradient solvent system of ethyl acetate and hexanes. Each product was analyzed by NMR.

Compound 755

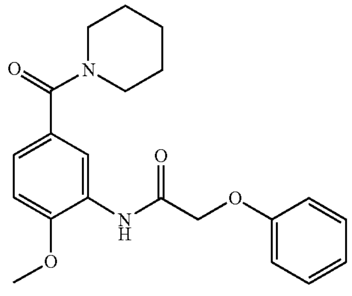

Chemical Formula: $C_{21}H_{24}N_2O_4$
Molecular Weight: 368.43

3-amino-4-methoxyphenyl)(piperidin-1-yl)methanone (0.3 g, 1.28 mmol) was added to DCM (10 ml) followed by the addition of triehtylamine (0.39 ml, 3.8 mmol) in a round bottom flask. Phenoxyacetyl chloride (0.18 ml, 1.2 mmol) was added to the reaction flask and allowed to stir at room temperature for 1 hour. $NaHCO_3$ was added to quench the reaction followed by extraction with DCM (20 ml×3 times). The organic layers were collected and dried using $MgSO_4$. The mixture was filtered and concentrated in vacuo. The product was purified through column chromatography to form yellow oil (101 mg, 21%)

$^1$H NMR (400 MHz, CDCl3) δ ppm 8.47 (d, 1H), 7.33-7.29 (m, 2H), 7.24-7.20 (m, 1H), 7.18-6.95 (m, 3H), 6.89-6.86 (d, 1H), 4.59 (s, 2H), 3.86 (s, 3H), 3.67-3.36 (m, 4H), 1.63-1.58 (m, 6H)

$^{13}$C NMR (400 MHz, CDCl3) δ ppm 170.783, 169.815, 166.221, 157.728, 157.109, 149.070, 129.833, 129.043, 126.209, 123.935, 122.364, 121.171, 118.747, 114.913, 110.110, 67.767, 56.071, 53.483, 24.652

Compound 757

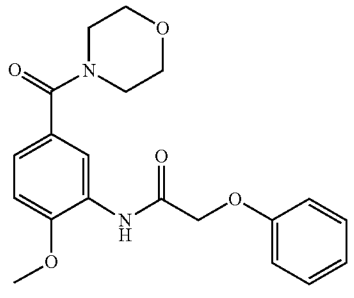

Chemical Formula: $C_{20}H_{22}N_2O_5$
Molecular Weight: 370.40

(3-amino-4-methoxyphenyl)(morpholino)methanone (0.15 g, 0.73 mmol) was added to DCM (10 ml) followed by the addition of triethylamine (0.41 ml, 2.91 mmol) in a round bottom flask. Phenoxyacetyl chloride (0.1 ml, 0.65 mmol) was added to the reaction flask and allowed to stir at room temperature for 1 hour. $NaHCO_3$ was added to quench the reaction followed by extraction with DCM (20 ml×3 times). The organic layers were collected and dried using $MgSO_4$. The mixture was filtered and concentrated in vacuo. The product was purified through column chromatography to form yellow crystals (112 mg, 42%)

$^1$H NMR (400 MHz, CDCl3) δ ppm 8.98 (s, 1H), 8.49-8.48 (s, 1H), 7.35-7.31 (m, 2H), 7.24-7.22 (m, 1H), 7.05-6.90 (m, 4H), 4.61 (s, 2H), 3.89 (s, 3H), 3.69 (s, 8H)

$^{13}$C NMR (400 MHz, CDCl3) δ ppm 169.950, 166.353, 157.079, 149.425, 129.862, 127.793, 126.312, 124.340, 122.421, 119.019, 114.913, 110.220, 67.756, 66.892, 56.113, 53.464

Compound 758

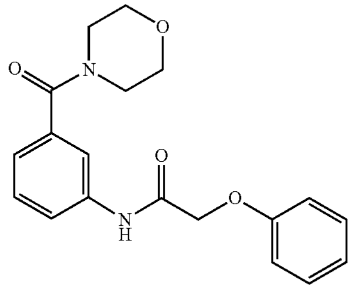

Chemical Formula: $C_{19}H_{20}N_2O_4$
Molecular Weight: 340.37

(3-aminophenyl)(morpholino)methanone (0.25 g, 1.21 mmol) was added to DCM (10 ml) followed by the addition of triehtylamine (0.61 ml, 4.36 mmol) in a round bottom flask. Phenoxyacetyl chloride (0.15 ml, 1.09 mmol) was added to the reaction flask and allowed to stir at room temperature for 1 hour. $NaHCO_3$ was added to quench the reaction followed by extraction with DCM (20 ml×3 times). The organic layers were collected and dried using $MgSO_4$. The mixture was filtered and concentrated in vacuo. The product was purified through column chromatography to form yellow crystals (145 mg, 35%)

$^1$H NMR (400 MHz, CDCl3) δ ppm 7.62 (s, 1H), 7.58-7.56 (d, 2H), 7.29-7.25 (t, 3H), 7.24-7.23 (d, 1H), 7.08-6.95 (m, 1H), 6.91-6.88 (dd, 2H), 4.51-4.50 (d, 2H), 3.65-3.37 (m, 8H)

$^{13}C$ NMR (400 MHz, CDCl3) δ ppm 169.687, 166.579, 156.985, 137.221, 136.120, 129.914, 129.353, 123.279, 122.498, 121.483, 118.972, 114.833, 67.559, 66.837, 60.377, 53.486, 21.037, 14.199.

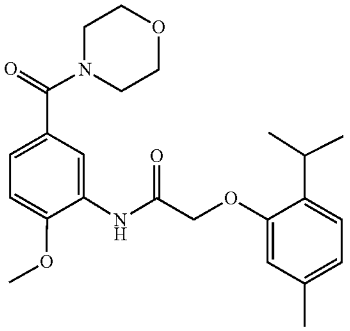

Chemical Formula: $C_{24}H_{30}N_2O_5$
Molecular Weight: 426.51

2-isopropyl-5-methylphenyl hydrogen carbonate (0.3 g, 1.44 mmol) was added to DCM (2 ml) followed by the addition of thionyl chloride (4 ml) in a round bottom flask. This solution was stirred for 4 hrs, and then evaporated. The evaporated flask was then diluted with 4 ml of DCM and then added to a solution of (3-amino-4-methoxyphenyl)(morpholino)methanone (0.3 g, 1.45 mmol) and in DCM (10 ml) and triethylamine (0.8 ml, 5.81 mmol). $NaHCO_3$ was added to quench the reaction followed by extraction with DCM (20 ml×3 times). The organic layers were collected and dried using $MgSO_4$. The mixture was filtered and concentrated in vacuo. The product was purified through column chromatography to form yellow oil (89 mg, 14%)

$^{1}H$ NMR (400 MHz, CDCl3) δ ppm 8.52 (s, 1H), 7.74-7.73 (s, 1H), 7.63-7.61 (d, 1H), 7.34-7.23 (m, 4H), 7.02-7.01 (t, 1H), 6.99-6.92 (d, 2H), 4.56 (s, 2H), 3.60-3.566 (t, 2H), 3.42-3.39 (t, 2H), 1.99 (s, 1H), 1.92-1.87 (m, 4H), 1.23-1.19 (t, 1H)

$^{13}C$ NMR (400 MHz, CDCl3) δ ppm 168.960, 166.525, 157.024, 138.026, 136.948, 129.890, 129.053, 123.355, 122.432, 121.386, 118.985, 114.822, 67.556, 60.375, 49.598, 46.250, 26.383, 24.436, 21.039, 14.199

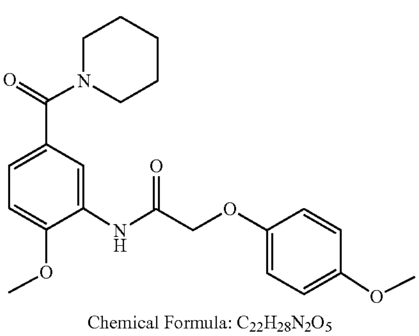

Chemical Formula: $C_{22}H_{28}N_2O_5$
Molecular Weight: 398.45

2-(4-methoxyphenoxy) acetic acid (0.3 g, 1.44 mmol) was added to DCM (2 ml) followed by the addition of thionyl chloride (4 ml) in a round bottom flask. This solution was stirred for 4 hrs, and then evaporated. The evaporated flask was then diluted with 4 ml of DCM and then added to a solution of 3-amino-4-methoxyphenyl)(piperidin-1-yl) methanone (0.3 g, 1.28 mmol) and in DCM (10 ml) and triethylamine (0.79 ml, 5.64 mmol). $NaHCO_3$ was added to quench the reaction followed by extraction with DCM (20 ml×3 times). The organic layers were collected and dried using $MgSO_4$. The mixture was filtered and concentrated in vacuo. The product was purified through column chromatography to form white crystals (136 mg, 12%)

$^{1}H$ NMR (400 MHz, CDCl3) δ ppm 8.97 (s, 1H), 8.47 (s, 1H), 7.24-7.18 (m, 2H), 6.92-6.83 (m, 5H), 4.54 (s, 2H), 3.87 (s, 3H), 3.75 (s, 3H), 3.57-3.52 (s, 3H), 1.79 (s, 7H)

$^{13}C$ NMR (400 MHz, CDCl3) δ ppm 169.855, 166.520, 154.965, 151.316, 149.088, 128.939, 126.212, 123.988, 121.789, 118.755, 116.070, 114.901, 110.095, 68.747, 56.062, 55.720, 26.045, 25.996, 25.964, 24.655

Compound 765

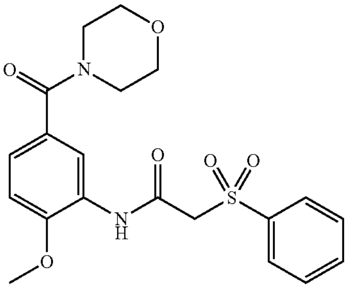

Chemical Formula: $C_{20}H_{22}N_2O_6S$
Molecular Weight: 418.46

N-(2-methoxy-5-(morpholine-4-carbonyl)phenyl)-2-(phenylthio)acetamide (140 mg, 0.362 mmol) was dissolved in DCM (10 ml). This mixture was cooled down to 0° C. and MCPBA (63 mg, 0.36 mmol) was added slowly to the reaction vessel and allowed to stir for 3 hours. The reaction mixture was then diluted with DCM and quenched with $NaHCO_3$ (5 ml). This reaction mixture was extracted with DCM (3×20 ml). The organic phase was collected and combined, dried with $MgSO_4$, filtered and concentrated in vacuo. The resulting mixture was purified by column chromatography to yield a beige solid (20 mg, 14%)

$^{1}H$ NMR (400 MHz, CDCl3) δ ppm 9.03 (s, 1H), 8.26 (s, 1H), 7.92-7.90 (d, 2H), 7.69-7.65 (m, 1H), 7.55-7.53 (m, 2H), 7.25-7.22 (m, 2H), 6.95-6.93 (d, 1H), 4.15 (s, 2H), 3.97 (s, 3H), 3.66-3.65 (s, 8H)

$^{13}C$ NMR (400 MHz, CDCl3) δ ppm 169.82, 158.36, 149.56, 138.04, 134.67, 129.62, 128.22, 127.75, 126.45, 124.74, 119.28, 110.29, 66.86, 63.08, 56.24.

Compound 765

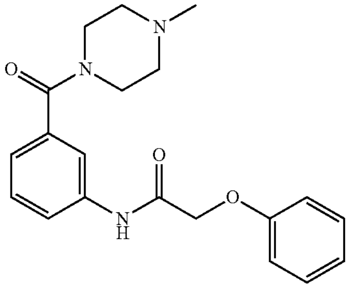

Chemical Formula: $C_{20}H_{23}N_3O_3$
Molecular Weight: 353.41

Amine (0.05 g, 0.23 mmol) was added to DCM (10 ml) followed by the addition of triehtylamine (0.13 ml, 0.91 mmol) in a round bottom flask. Phenoxyacetyl chloride (0.03 ml, 0.21 mmol) was added to the reaction flask and allowed to stir at room temperature for 1 hour. $NaHCO^3$ was added to quench the reaction followed by extraction with DCM (20 ml×3 times). The organic layers were collected and dried using $MgSO^4$. The mixture was filtered and concentrated in vacuo. The product was purified through column chromatography to form brown oil (39 mg, 49%)

$^1$H NMR (400 MHz, CDCl3) δ ppm 7.64-7.61 (m, 2H), 7.36-7.29 (m, 3H), 7.14-7.12 (d, 1H), 7.04-6.94 (m, 3H), 4.57 (s, 2H), 3.78-3.76 (m, 1H), 3.47 (s, 2H), 2.52-2.45 (m, 4H), 2.25 (s, 3H)

$^{13}$C NMR (400 MHz, CDCl3) δ ppm 169.588, 166.545, 156.939, 137.106, 136.389, 129.941, 129.363, 123.341, 122.551, 121.398, 118.877, 114.832, 67.548, 60.389, 53.433, 45.548, 29.695, 21.037, 14.194

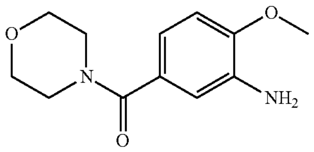

Chemical Formula: $C_{12}H_{16}N_2O_3$
Molecular Weight: 236.27

4-methoxy-3-aminobenzoic acid (2.1 g, 12.7 mmol) was added to DCM (15 ml) followed by the addition of triehtylamine (3.2 ml, 23 mmol) in a round bottom flask. EDCI.HCL (3.3 g, 17.3 mmol) was added to the reaction and the solution was allowed to stir for 40 minutes. Morpholine (1.0 ml, 11.5 mmol) was added to the reaction flask and allowed to stir at room temperature for 24 hours. $NaHCO_3$ was added to quench the reaction followed by extraction with DCM (20 ml×3 times). The organic layers were collected and dried using $MgSO_4$. The mixture was filtered and concentrated in vacuo. The product was purified through column chromatography to form white crystals (1.6 g, 44%)

$^1$H NMR (400 MHz, CDCl3) δ ppm) 6.77-6.74 (m, 3H), 3.83 (s, 3H), 3.64 (s, 8H), 2.01 (s, 1H), 1.24-1.21 (t, 1H)

$^{13}$C N M R (400 MHz, CDCl3) δ ppm) 170.781, 148.495, 136.184, 127.876, 117.777, 113.920, 109.740, 66.966, 55.582

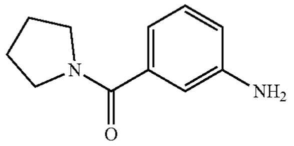

Chemical Formula: $C_{11}H_{14}N_2O$
Molecular Weight: 190.24

3-aminobenzoic acid (1 g, 7.99 mmol) was added to DCM (15 ml) followed by the addition of triehtylamine (4.06 ml, 29.16 mmol) in a round bottom flask. EDCI.HCL (1.82 g, 9.47 mmol) was added to the reaction and the solution was allowed to stir for 40 minutes. Pyrrolidine (0.53 ml, 6.56 mmol) was added to the reaction flask and allowed to stir at room temperature for 24 hours. $NaHCO_3$ was added to quench the reaction followed by extraction with DCM (20 ml×3 times). The organic layers were collected and dried using $MgSO_4$. The mixture was filtered and concentrated in vacuo. The product was purified through column chromatography to form clear oil (0.645 g, 57.1%)

$^1$H NMR (400 MHz, CDCl3) δ ppm 7.13-7.09 (t, 1H), 6.81-6.68 (m, 2H), 6.66-6.65 (d, 1H), 3.71-3.69 (s, 1H), 3.59-3.56 (t, 2H), 3.39-3.36 (t, 2H)

$^{13}$C NMR (400 MHz, CDCl3) δ ppm 169.972, 146.841, 138.148, 128.982, 116.414, 116.202, 113.428, 53.586, 49.475, 45.998, 26.234, 24.387

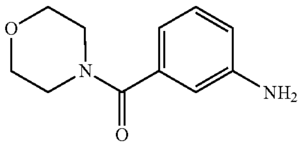

Chemical Formula: $C_{11}H_{14}N_2O_2$
Molecular Weight: 206.24

3-aminobenzoic acid (1 g, 7.29 mmol) was added to DCM (15 ml) followed by the addition of triehtylamine (3 ml, 21.8 mmol) in a round bottom flask. EDCI.HCL (1.7 g, 10.2 mmol) was added to the reaction and the solution was allowed to stir for 40 minutes. Morpholine (0.57 ml, 26.6 mmol) was added to the reaction flask and allowed to stir at room temperature for 24 hours. $NaHCO_3$ was added to quench the reaction followed by extraction with DCM (20 ml×3 times). The organic layers were collected and dried using $MgSO_4$. The mixture was filtered and concentrated in vacuo. The product was purified through column chromatography to form white crystals (1.1 g, 73%)

$^1$H NMR (400 MHz, CDCl3) δ ppm) 6.54-6.52 (s, 3H), 3.83 (s, 2H), 3.57-3.29 (m, 8H)

$^{13}$C NMR (400 MHz, CDCl3) δ ppm) 170.723, 147.233, 136.173, 129.307, 116.212, 116.155, 113.211, 66.786, 48.130, 48.096, 48.080, 42.441, 42.413

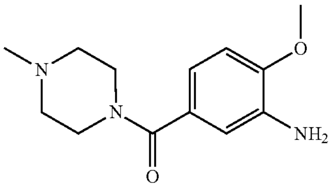

Chemical Formula: $C_{13}H_{19}N_3O_2$
Molecular Weight: 249.31

4-methoxy-3-aminobenzoic acid (1 g, 5.98 mmol) was added to DCM (15 ml) followed by the addition of triehtylamine (3.34 ml, 23.93 mmol) in a round bottom flask. EDCI.HCL (1.7 g, 8.97 mmol) was added to the reaction and the solution was allowed to stir for 40 minutes. 1-methylpiperizine (0.60 ml, 5.38 mmol) was added to the reaction flask and allowed to stir at room temperature for 24 hours. $NaHCO_3$ was added to quench the reaction followed by extraction with DCM (20 ml×3 times). The organic layers were collected and dried using $MgSO_4$. The mixture was filtered and concentrated in vacuo. The product was purified through column chromatography to form beige crystals (554 mg, 42.6%)

$^1$H NMR (400 MHz, CDCl3) δ ppm 6.63-6.60 (m, 3H), 3.85 (m, 2H), 3.73-3.7 (m, 3H), 3.51-3.48 (m, 4H), 3.26-3.25 (m, 1H), 2.26 (s, 3H), 2.18-2.17 (m, 3H)

$^{13}C$ NMR (400 MHz, CDCl3) δ ppm 13C NMR (400 MHz, CDCl3) δ ppm 170/83, 148.25, 143.17, 129.40, 128.35, 114.21, 111.32, 54.91, 45.76, 45.75

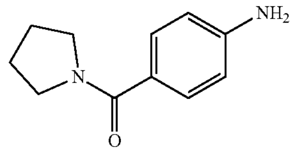

Chemical Formula: $C_{11}H_{14}N_2O$
Molecular Weight: 190.24

4-aminobenzoic acid (1 g, 7.99 mmol) was added to DCM (15 ml) followed by the addition of triehtylamine (4.06 ml, 29.16 mmol) in a round bottom flask. EDCI.HCL (1.82 g, 9.47 mmol) was added to the reaction and the solution was allowed to stir for 40 minutes. Pyrrolidine (0.53 ml, 6.56 mmol) was added to the reaction flask and allowed to stir at room temperature for 24 hours. $NaHCO_3$ was added to quench the reaction followed by extraction with DCM (20 ml×3 times). The organic layers were collected and dried using $MgSO_4$. The mixture was filtered and concentrated in vacuo. The product was purified through column chromatography to form clear oil (0.645 g, 57.1%)

$^{1}H$ NMR (400 MHz, CDCl3) δ ppm 7.13-7.09 (t, 1H), 6.81-6.68 (m, 2H), 6.66-6.65 (d, 1H), 3.71-3.69 (s, 1H), 3.59-3.56 (t, 2H), 3.39-3.36 (t, 2H)

$^{13}C$ NMR (400 MHz, CDCl3) δ ppm 169.972, 146.841, 138.148, 128.982, 116.414, 116.202, 113.428, 53.586, 49.475, 45.998, 26.234, 24.387

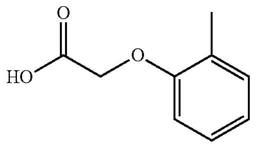

Chemical Formula: $C_9H_{10}O_3$
Molecular Weight: 166.17

This compound was prepared following general procedure 3 using o-cresol (14.3 g, 133 mmol), chloroacetic acid (11.5 g, 121 mmol), and NaOH (14.5 g, 364 mmol) in distilled H2O (50 mL). Crude product (7 g) was purified by recrystallization using EtOAc and hexanes resulting in 2-(otolyloxy)acetic acid, a white powder (3 g, 15%, Rf=0.6 in 3:2 Hexanes:EtOAc).

$^{1}H$ NMR (400 MHz; CDCl3): δ 7.21-7.18 (m, 2H), 6.98-6.96 (t, J=7.2, 1H), 6.76 (d, J=8.0, 1H), 4.72 (s, 2H), 2.32 (s, 3H)

$^{13}C$ NMR: (400 MHz; CDCl3): δ 131.68, 127.69, 127.35, 122.41, 111.80, 65.59, 16.64

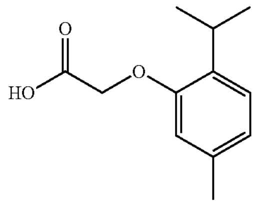

Chemical Formula: $C_{12}H_{16}O_3$
Molecular Weight: 208.25

This compound was prepared following general procedure 3 using Thymol (34.9 g. 232.8 mmol), chloroacetic acid (20 g, 211.7 mmol), and NaOH (25.4 g, 635 mmol) in distilled $H_2O$ (75 mL).

No purification was required for this reaction. Pure product, 2-(2-isopropyl-5methylphenoxy)acetic acid, a beigh powder (14.23 g, 32%, Rf=0.57 in 3:2 EtOAc:Hexanes).

$^{1}H$ NMR (400 MHz; CDCl3): δ 7.15 (d, J=7.7, 1H), 6.83 (d, J=7.7, 1H), 6.58 (s, 1H), 4.70 (s, 2H), 3.36 (7, J=6.9, 1H), 2.33 (s, 3H), 1.24 (d, J=6.9, 6H)

$^{13}C$ NMR: (400 MHz; CDCl3): δ 174.85, 155.01, 136.91, 135.01, 126.85, 123.12, 112.84, 65.63, 27.03, 23.25, 21.74

Example 4: Bioassay of Small Molecule Inhibitors of SOX9

The screen relied on a SOX9 reporter construct that has 4 repeats of the SOX9 binding site coupled to the mouse Col2a1 minimal promoter (−89 to +6) cloned upstream of a luciferase gene in the plasmid pGL4 (Promega). Stably transfected ATDC5 SOX9 reporter clones were selected and characterized. In these clones luciferase activity is a convenient and very sensitive read-out for SOX9 activity. Compounds were assayed at 10 μM concentrations. A reduction in luciferase activity was indicative of SOX9 inhibition. The results are shown in FIGS. 7-10.

Some of the inhibitor compounds were also tested on ATDC5 cells for their effect on SOX9 target gene expression by q-PCR (aggrecan data is shown in FIG. 11) and on LX-2 (human hepatocyte (stellate cells) cells for collagen gene expression (associated with liver fibrosis), as shown in FIG. 12.

These results demonstrate the activity of the compounds tested as effective inhibitors of SOX9, similar to compound 1. This is indicative of the usefulness of these compounds in the treatment of conditions that would benefit from a reduction in SOX9 activity or expression.

REFERENCES

1. Morgenstern, D. A., Asher, R. A. & Fawcett, J. W. Chondroitin sulphate proteoglycans in the CNS injury response. Prog. Brain Res. 137, 313-332 (2002).
2. Gotting, C., Kuhn, J., Zahn, R., Brinkmann, T. & Kleesiek, K. Molecular cloning and expression of human UDP-d-Xylose:proteoglycan core protein beta-d-xylosyltransferase and its first isoform XT-II. J. Mol. Biol. 304, 517-528 (2000).
3. Yamauchi, S., et al. Molecular cloning and expression of chondroitin 4-sulfotransferase. J. Biol. Chem. 275, 8975-8981 (2000).
4. Celio, M. R. & Blumcke, I. Perineuronal nets—a specialized form of extracellular matrix in the adult nervous system. Brain Res. Brain Res. Rev. 19, 128-145 (1994).

5. Galtrey, C. M. & Fawcett, J. W. The role of chondroitin sulfate proteoglycans in regeneration and plasticity in the central nervous system. Brain Res Rev 54, 1-18 (2007).
6. Bignami, A., Asher, R. & Perides, G. The extracellular matrix of rat spinal cord: a comparative study on the localization of hyaluronic acid, glial hyaluronate-binding protein, and chondroitin sulfate proteoglycan. Exp. Neurol. 117, 90-93. (1992).
7. Lemons, M. L., Howland, D. R. & Anderson, D. K. Chondroitin sulfate proteoglycan immunoreactivity increases following spinal cord injury and transplantation. Exp. Neurol. 160, 51-65. (1999).
8. McKeon, R. J., Schreiber, R. C., Rudge, J. S. & Silver, J. Reduction of neurite outgrowth in a model of glial scarring following CNS injury is correlated with the expression of inhibitory molecules on reactive astrocytes. J. Neurosci. 11, 3398-3411. (1991).
9. Zuo, J., Neubauer, D., Dyess, K., Ferguson, T. A. & Muir, D. Degradation of chondroitin sulfate proteoglycan enhances the neurite—promoting potential of spinal cord tissue. Exp. Neurol. 154, 654-662. (1998).
10. Meiners, S., Powell, E. M. & Geller, H. M. A distinct subset of tenascin/CS-6-PG-rich astrocytes restricts neuronal growth in vitro. J. Neurosci. 15, 8096-8108 (1995).
11. Dou, C. L. & Levine, J. M. Inhibition of neurite growth by the NG2 chondroitin sulfate proteoglycan. J. Neurosci. 14, 7616-7628 (1994).
12. Schmalfeldt, M., Bandtlow, C. E., Dours-Zimmermann, M. T., Winterhalter, K. H. & Zimmermann, D. R. Brain derived versican V2 is a potent inhibitor of axonal growth. J. Cell Sci. 113 (Pt 5), 807-816 (2000).
13. Friedlander, D. R., et al. The neuronal chondroitin sulfate proteoglycan neurocan binds to the neural cell adhesion molecules Ng-CAM/L1/NILE and N-CAM, and inhibits neuronal adhesion and neurite outgrowth. J. Cell Biol. 125, 669-680 (1994).
14. Yamada, H., et al. The brain chondroitin sulfate proteoglycan brevican associates with astrocytes ensheathing cerebellar glomeruli and inhibits neurite outgrowth from granule neurons. J. Neurosci. 17, 7784-7795 (1997).
15. Milev, P., et al. Interactions of the chondroitin sulfate proteoglycan phosphacan, the extracellular domain of a receptor-type protein tyrosine phosphatase, with neurons, glia, and neural cell adhesion molecules. J. Cell Biol. 127, 1703-1715 (1994).
16. Bradbury, E. J., et al. Chondroitinase ABC promotes functional recovery after spinal cord injury. Nature 416, 636-640. (2002).
17. Caggiano, A. O., Zimber, M. P., Ganguly, A., Blight, A. R. & Gruskin, E. A. Chondroitinase ABCI improves locomotion and bladder function following contusion injury of the rat spinal cord. J. Neurotrauma 22, 226-239 (2005).
18. Corvetti, L. & Rossi, F. Degradation of chondroitin sulfate proteoglycans induces sprouting of intact purkinje axons in the cerebellum of the adult rat. J. Neurosci. 25, 7150-7158 (2005).
19. Garcia-Alias, G., Barkhuysen, S., Buckle, M. & Fawcett, J. W. Chondroitinase ABC treatment opens a window of opportunity for task-specific rehabilitation. Nat. Neurosci. 12, 1145-1151 (2009).
20. Huang, W. C., et al. Chondroitinase ABC promotes axonal re-growth and behavior recovery in spinal cord injury. Biochem. Biophys. Res. Commun. 349, 963-968 (2006).
21. Ikegami, T., et al. Chondroitinase ABC combined with neural stem/progenitor cell transplantation enhances graft cell migration and outgrowth of growth-associated protein-43-positive fibers after rat spinal cord injury. Eur. J. Neurosci. 22, 3036-3046 (2005).
22. Karimi-Abdolrezaee, S., Eftekharpour, E., Wang, J., Schut, D. & Fehlings, M. G. Synergistic effects of transplanted adult neural stem/progenitor cells, chondroitinase, and growth factors promote functional repair and plasticity of the chronically injured spinal cord. J. Neurosci. 30, 1657-1676 (2010).
23. Wang, D., Ichiyama, R. M., Zhao, R., Andrews, M. R. & Fawcett, J. W. Chondroitinase combined with rehabilitation promotes recovery of forelimb function in rats with chronic spinal cord injury. J. Neurosci. 31, 9332-9344 (2011).
24. Grimpe, B. & Silver, J. A novel DNA enzyme reduces glycosaminoglycan chains in the glial scar and allows microtransplanted dorsal root ganglia axons to regenerate beyond lesions in the spinal cord. J. Neurosci. 24, 1393-1397 (2004).
25. Gris, P., Tighe, A., Levin, D., Sharma, R. & Brown, A. Transcriptional regulation of scar gene expression in primary astrocytes. Glia 55, 1145-1155 (2007).
26. Stolt, C. C., et al. The Sox9 transcription factor determines glial fate choice in the developing spinal cord. Genes Dev. 17, 1677-1689 (2003).
27. Akiyama, H., Chaboissier, M. C., Martin, J. F., Schedl, A. & de Crombrugghe, B. The transcription factor Sox9 has essential roles in successive steps of the chondrocyte differentiation pathway and is required for expression of Sox5 and Sox6. Genes Dev. 16, 2813-2828 (2002).
28. Hayashi, S. & McMahon, A. P. Efficient recombination in diverse tissues by a tamoxifen-inducible form of Cre: a tool for temporally regulated gene activation/inactivation in the mouse. Dev. Biol. 244, 305-318 (2002).
29. McKillop, W. M., Dragan, M., Schedl, A. & Brown, A. Conditional Sox9 ablation reduces chondroitin sulfate proteoglycan levels and improves motor function following spinal cord injury. Glia 61, 164-177 (2013).
30. Basso, D. M., et al. Basso Mouse Scale for locomotion detects differences in recovery after spinal cord injury in five common mouse strains. J. Neurotrauma 23, 635-659 (2006).
31. McKillop, W. M., et al. Conditional Sox9 ablation improves locomotor recovery after spinal cord injury by increasing reactive sprouting. Exp. Neurol. 283, 1-15 (2016).
32. Peterson, J. T. Matrix metalloproteinase inhibitor development and the remodeling of drug discovery. Heart failure reviews 9, 63-79 (2004).
33. Pizzi, M. A. & Crowe, M. J. Matrix metalloproteinases and proteoglycans in axonal regeneration. Exp. Neurol. 204, 496-511 (2007).
34. Xu, X., et al. Sox9 knockout mice have improved recovery following stroke. Exp.
Neurol. (2018).
35. Athwal, V. S., et al. SOX9 predicts progression toward cirrhosis in patients while its loss protects against liver fibrosis. EMBO Mol Med 9, 1696-1710 (2017).
36. Rey-Rico, A., et al. Effective Remodelling of Human Osteoarthritic Cartilage by sox9 Gene Transfer and Overexpression upon Delivery of rAAV Vectors in Polymeric Micelles. Mol Pharm 15, 2816-2826 (2018).
37. Cucchiarini, M., et al. Restoration of the extracellular matrix in human osteoarthritic articular cartilage by overexpression of the transcription factor SOX9. Arthritis Rheum. 56, 158-167 (2007).

38. Wagner, T., et al. Autosomal sex reversal and campomelic dysplasia are caused by mutations in and around the SRY-related gene SOX9. Cell 79, 1111-1120 (1994).
39. Bernard, P., et al. Dimerization of SOX9 is required for chondrogenesis, but not for sex determination. Hum. Mol. Genet. 12, 1755-1765 (2003).
40. Sock, E., et al. Loss of DNA-dependent dimerization of the transcription factor SOX9 as a cause for campomelic dysplasia. Hum. Mol. Genet. 12, 1439-1447 (2003).
41. Coustry, F., et al. The dimerization domain of SOX9 is required for transcription activation of a chondrocyte-specific chromatin DNA template. Nucleic Acids Res 38, 6018-6028 (2010).
42. Schwarze, S. R., Ho, A., Vocero-Akbani, A. & Dowdy, S. F. In vivo protein transduction: delivery of a biologically active protein into the mouse. Science 285, 1569-1572 (1999).
43. Murtha, L. A., et al. Cerebrospinal fluid is drained primarily via the spinal canal and olfactory route in young and aged spontaneously hypertensive rats. Fluids Barriers CNS 11, 12 (2014).
44. Simon, M. J. & Iliff, J. J. Regulation of cerebrospinal fluid (CSF) flow in neurodegenerative, neurovascular and neuroinflammatory disease. Biochim. Biophys. Acta 1862, 442-451 (2016).
45. Basso, D. M., Beattie, M. S. & Bresnahan, J. C. A sensitive and reliable locomotor rating scale for open field testing in rats. J. Neurotrauma 12, 1-21. (1995).
46. Rolls, A., et al. Two faces of chondroitin sulfate proteoglycan in spinal cord repair: a role in microglia/macrophage activation. PLoS Med 5, e171 (2008).
47. Shukunami, C., Ohta, Y., Sakuda, M. & Hiraki, Y. Sequential progression of the differentiation program by bone morphogenetic protein-2 in chondrogenic cell line ATDC5. Exp. Cell Res. 241, 1-11 (1998).
48. Weston, A. D., Chandraratna, R. A., Torchia, J. & Underhill, T. M. Requirement for RAR-mediated gene repression in skeletal progenitor differentiation. J. Cell Biol. 158, 39-51 (2002).
49. Hanover, J. A., Love, D. C. & Prinz, W. A. Calmodulin-driven nuclear entry: trigger for sex determination and terminal differentiation. J. Biol. Chem. 284, 12593-12597 (2009).
50. McFadden, M. J., Hryciw, T., Brown, A., Junop, M. S. & Brennan, J. D. Evaluation of the calmodulin-SOX9 interaction by "magnetic fishing" coupled to mass spectrometry. Chembiochem 15, 2411-2419 (2014).
51. Xue Y, Lian W, Zhi J, Yang W, Li Q, Guo X, Gao J, Qu H, Lin W, Li Z, Lai L, Wang Q. HDAC5-mediated deacetylation and nuclear localisation of SOX9 is critical for tamoxifen resistance in breast cancer. BrJ Cancer (November 2019).
52. Voronkova M A, Rojanasakul L W, Kiratipaiboon C, Rojanasakul Y. SOX9-ALDH axis determines resistance to chemotherapy in non-small cell lung cancer. Mol Cell Biol. (October 2019).
53. Hiraoka K, Hayashi T, Kaneko R, Nasu-Nishimura Y, Koyama-Nasu R, Kawasaki Y, Akiyama T. SOX9-mediated upregulation of LGR5 is important for glioblastoma tumorigenicity. Biochem Biophys Res Commun. 460(2), 216-21 (2015).
54. Francis J C, Capper A, Ning J, Knight E, de Bono J, Swain A. SOX9 is a driver of aggressive prostate cancer by promoting invasion, cell fate and cytoskeleton alterations and epithelial to mesenchymal transition. Oncotarget. 9(7), 7604-7615 (2018).

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A pharmaceutical composition comprising a SOX9 dimerization inhibitor and a pharmaceutically acceptable diluent, carrier or excipient, wherein the SOX9 inhibitor is:

an inhibitor compound of formula I:

I

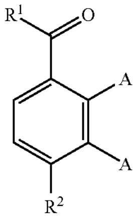

where:

$R^1$ is $NR^7R^8$, wherein $R^7$ and $R^8$ are each independently a straight or branched $C_1$ to $C_6$ alkyl, or $R^7$ and $R^8$, together with the N atom to which they are attached, form a heterocyclyl containing one or two heteroatoms selected from N and O, which is optionally substituted with an alkyl;

$R^2$ is H, a $C_1$ to $C_6$ alkyl, a $C_1$ to $C_6$ alkoxy, or halo; and one A is H and the other is:

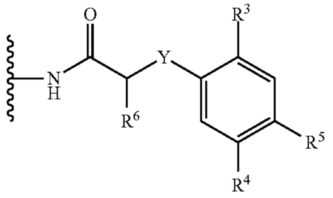

where:

$R^3$ is H or a $C_2$ to $C_6$ alkyl;

$R^4$ is H or a $C_1$ to $C_6$ alkyl;

$R^5$ is H, halo or $NCH_2C_6H_5$;

$R^6$ is H or methyl; and

Y is O or $SO_2$, or a pharmaceutically acceptable salt or solvate thereof.

2. The pharmaceutical composition of claim 1, wherein the SOX9 dimerization inhibitor is the inhibitor compound of formula I and wherein $R^1$ is piperazine, N-methylpiperazine, morpholine, piperidine, pyrrolidine or $N(C_1\text{-}C_6\ alkyl)_2$.

3. The pharmaceutical composition of claim 1, wherein $R^2$ is H, methyl, methoxy or Cl.

4. The pharmaceutical composition of claim 1, wherein $R^3$ is H or isopropyl.

5. The pharmaceutical composition of claim 1, wherein $R^4$ is H or methyl.

6. The pharmaceutical composition of claim 1, wherein $R^5$ is H, $C_1$ or $NCH_2C_6H_5$.

7. The pharmaceutical composition of claim 1, wherein $R^6$ is H.

8. The pharmaceutical composition of claim 1, wherein Y is O.

9. The pharmaceutical composition of claim 1, wherein the A in the ortho position relative to $R^1$ is H.

10. The pharmaceutical composition of claim 1, wherein the SOX9 dimerization inhibitor is a compound selected from the group consisting of

1

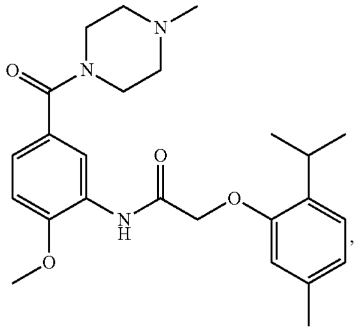

,

767

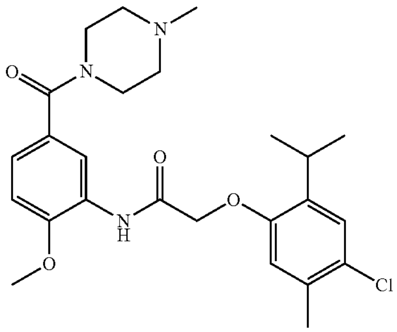

-continued
756
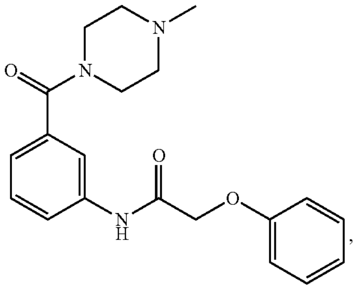
,
757
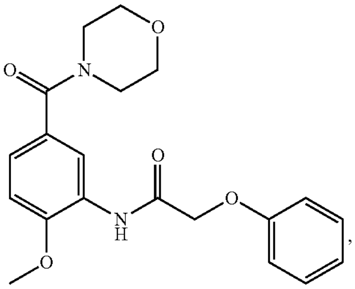
,
758
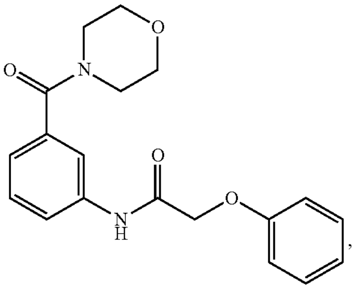
,
760
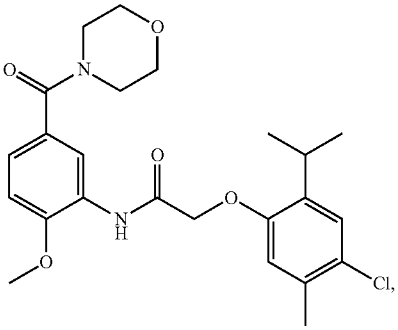
,
765
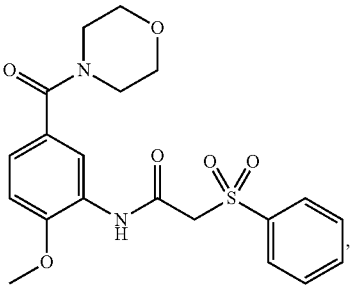
,
-continued
782
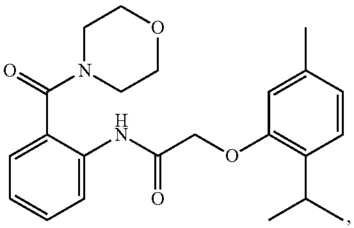
,
751
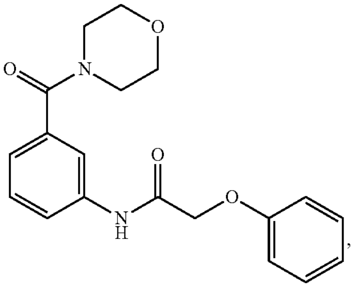
,
752
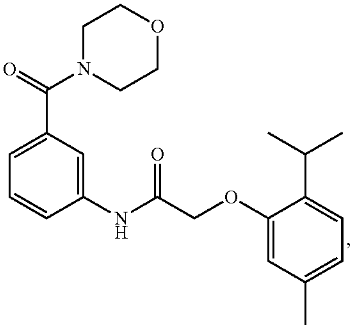
,
754
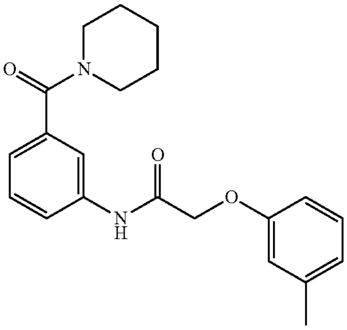
,
755
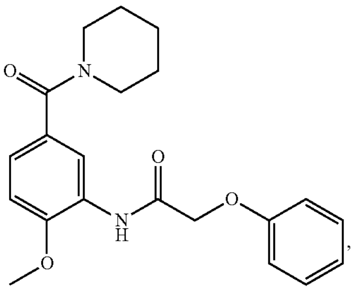
, -continued
768
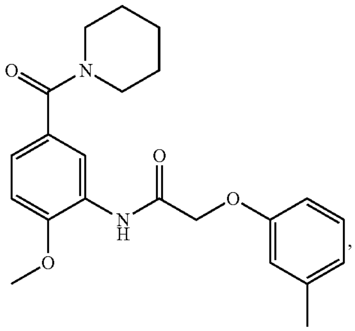
,
759
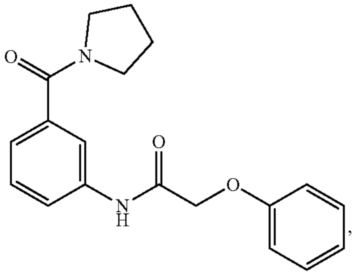
,
781
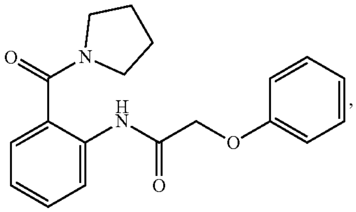
,
761
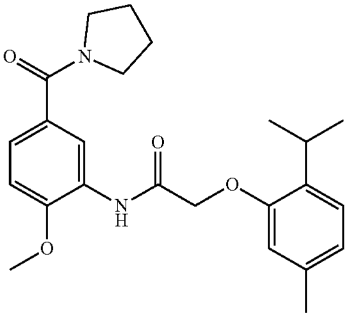
790
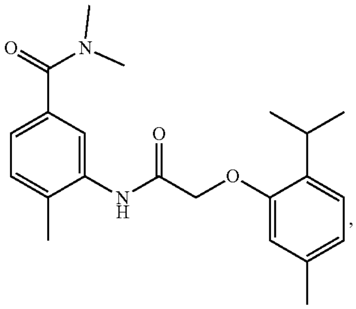
,
-continued
2
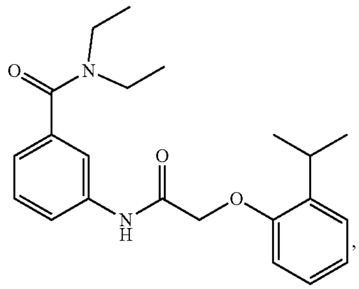
,
787
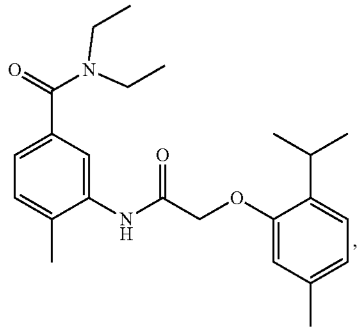
,
815
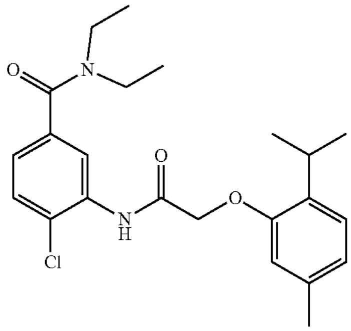
817
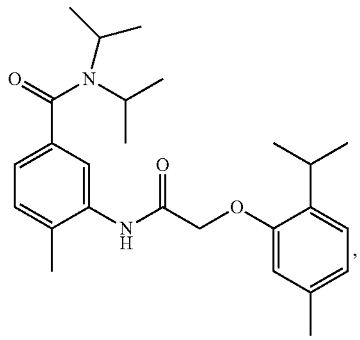
,
835
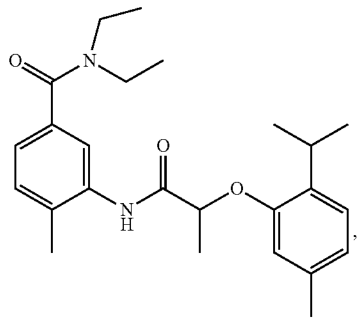
, -continued

844

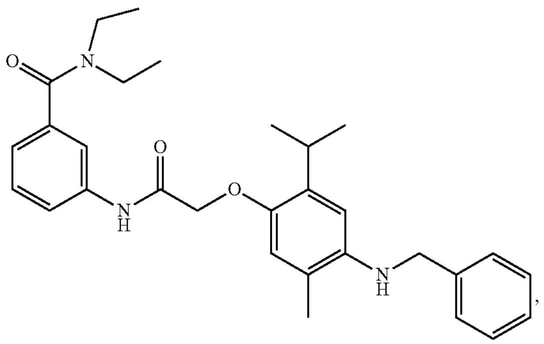

,

838

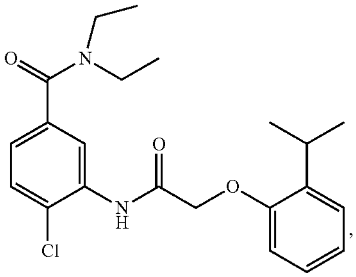

,

822

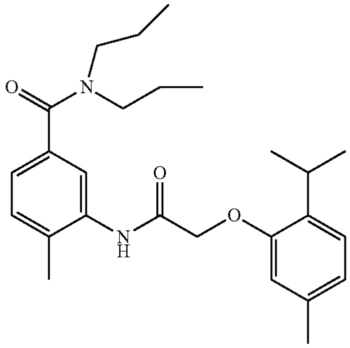

and

816

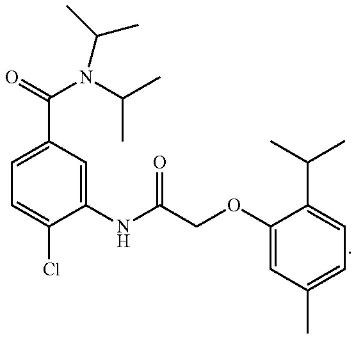

.

11. The pharmaceutical composition of claim 1 for use in treating a disease or condition characterized by increased dimeric SOX9 activity and/or increased CSPG expression, or a disease or disorder that may be ameliorated by decreasing dimeric SOX9 or CSPG activity.

12. The pharmaceutical composition of claim 11, wherein the disease or condition is a condition involving inhibited neuronal growth or neuronal plasticity, fibrotic disorders and cancer.

13. A SOX9 dimerization inhibitor that is:
a compound of formula I:

I

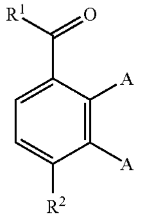

where:

$R^1$ is $NR^7R^8$, wherein $R^7$ and $R^8$ are each independently a straight or branched $C_1$ to $C_6$ alkyl, or $R^7$ and $R^8$, together with the N atom to which they are attached, form a heterocyclyl containing one or two heteroatoms selected from N and O, which is optionally substituted with an alkyl;

$R^2$ is H, a $C_1$ to $C_6$ alkyl, a $C_1$ to $C_6$ alkoxy, or halo; and one A is H and the other is:

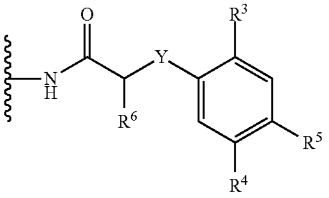

where:

$R^3$ is H or a $C_2$ to $C_6$ alkyl;

$R^4$ is H or a $C_1$ to $C_6$ alkyl;

$R^5$ is H, halo or $NCH_2C_6H_5$;

$R^6$ is H or methyl; and

Y is O or $SO_2$, or a pharmaceutically acceptable salt or solvate thereof, with the proviso that the compound is not

1

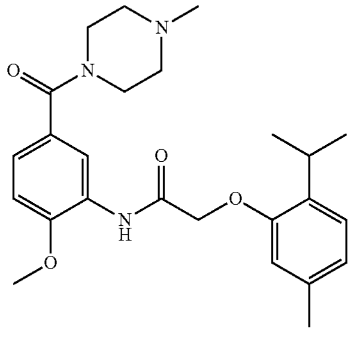

or

2

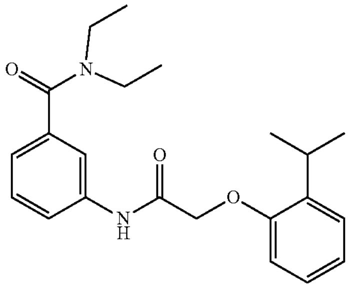

, and wherein when:

$R^2$, $R^3$, $R^4$, $R^5$ and $R^6$ are H and Y is O, then $R^1$ is not 4-methylpiperazyn-1-yl, morpholino, or pyrrol-1-yl;

$R^2$ is H or $OCH_3$, $R^3$, $R^5$ and $R^6$ are H, $R^4$ is $CH_3$ and Y is O, then $R^1$ is not piperidin-1-yl;

$R^2$, $R^5$ and $R^6$ are H, $R^3$ is isopropyl and $R^4$ is $CH_3$ and Y is O, then $R^1$ is not piperidin-1-yl, morpholino; and $R^5$ and $R^6$ are H, $R^3$ is isopropyl and $R^2$ and $R^4$ are $CH_3$ and Y is O, then $R^1$ is not $—N(CH_2CH_3)_2$.

* * * * *